United States Patent
de los Reyes

(10) Patent No.: US 9,120,037 B2
(45) Date of Patent: *Sep. 1, 2015

(54) STACKABLE PLANAR ADSORPTIVE DEVICES

(71) Applicant: SPF INNOVATIONS LLC, Somerville, MA (US)

(72) Inventor: Gaston de los Reyes, Somerville, MA (US)

(73) Assignee: SPF INNOVATIONS, LLC, Somerville, MA (US)

( * ) Notice: Subject to any disclaimer, the term of this patent is extended or adjusted under 35 U.S.C. 154(b) by 77 days.

This patent is subject to a terminal disclaimer.

(21) Appl. No.: 13/964,726

(22) Filed: Aug. 12, 2013

(65) Prior Publication Data

US 2014/0339170 A1    Nov. 20, 2014

Related U.S. Application Data

(63) Continuation-in-part of application No. 13/013,807, filed on Jan. 25, 2011, now Pat. No. 8,506,802.

(60) Provisional application No. 61/297,896, filed on Jan. 25, 2010.

(51) Int. Cl.
*B01D 15/20* (2006.01)
*B01D 15/22* (2006.01)
*G01N 30/52* (2006.01)
*G01N 30/60* (2006.01)

(52) U.S. Cl.
CPC .......... *B01D 15/206* (2013.01); *B01D 15/22* (2013.01); *G01N 30/52* (2013.01); *G01N 30/6047* (2013.01); *G01N 2030/527* (2013.01); *G01N 2030/528* (2013.01)

(58) Field of Classification Search
CPC .. B01D 15/206; B01D 15/22; G01N 30/6047; G01N 30/52; G01N 2030/527; G01N 2030/528
USPC ........... 210/635, 656, 658, 659, 198.2, 198.3, 210/264, 291
See application file for complete search history.

(56) References Cited

U.S. PATENT DOCUMENTS

| | | | |
|---|---|---|---|
| 8,506,802 B1 * | 8/2013 | de los Reyes | 210/198.2 |
| 2009/0321338 A1 | 12/2009 | Natarajan | |
| 2010/0187167 A1 | 7/2010 | Reinbigler et al. | |
| 2012/0097591 A1 | 4/2012 | Berthold et al. | |
| 2012/0118807 A1 | 5/2012 | Natarajan | |
| 2013/0068671 A1 | 3/2013 | Gebauer et al. | |

OTHER PUBLICATIONS

International Search Report KIPO as ISA mailed Nov. 20, 2014 (PCT/US2014/050743).
Written Opinion KIPO as ISA mailed Nov. 20, 2014 (PCT/US2014/050743).

* cited by examiner

*Primary Examiner* — Ernest G Therkorn
(74) *Attorney, Agent, or Firm* — Barry Gaiman

(57) ABSTRACT

Adsorptive bed devices include a scaffold in housing having a stress absorbing rigid structure and open cells filled with adsorptive beads. The scaffold restricts movement of the plurality of adsorptive beads, absorbs compressive stress induced by a hydraulic pressure gradient along a direction of liquid flow and transfers a portion of the induced compressive stress to the housing. In one embodiment the adsorptive bed in packed into a chromatography column, and in another embodiment the adsorptive bed is sealed in a monolithic block.

16 Claims, 24 Drawing Sheets

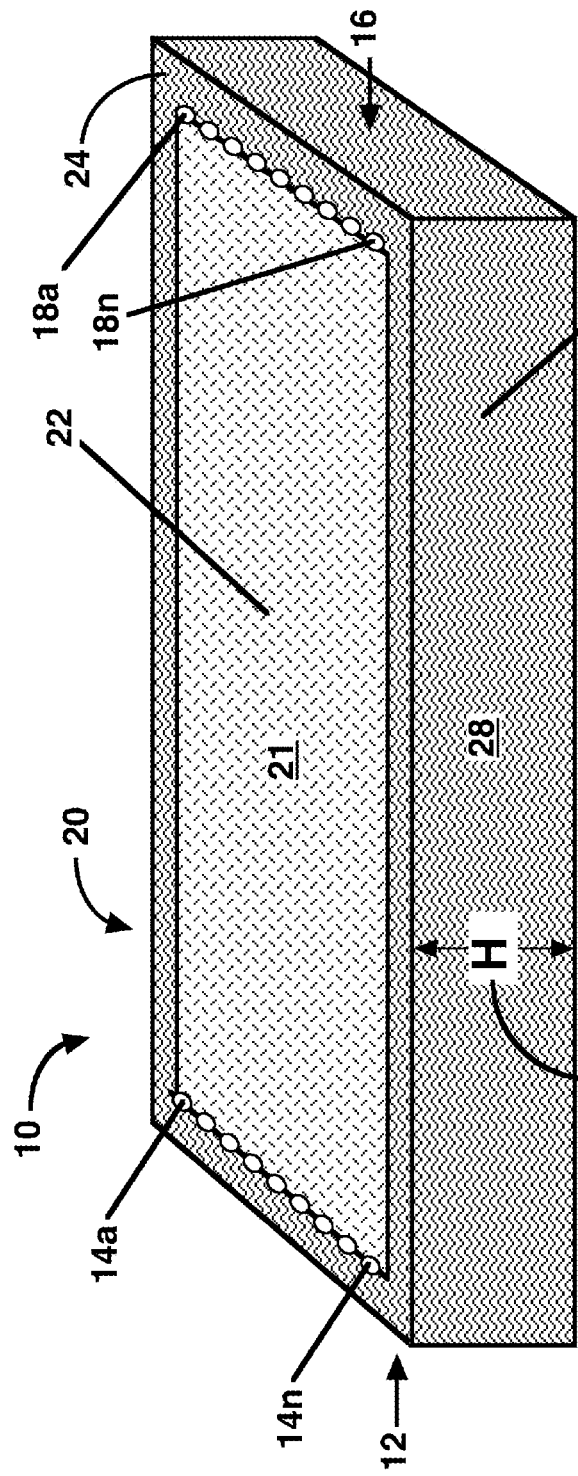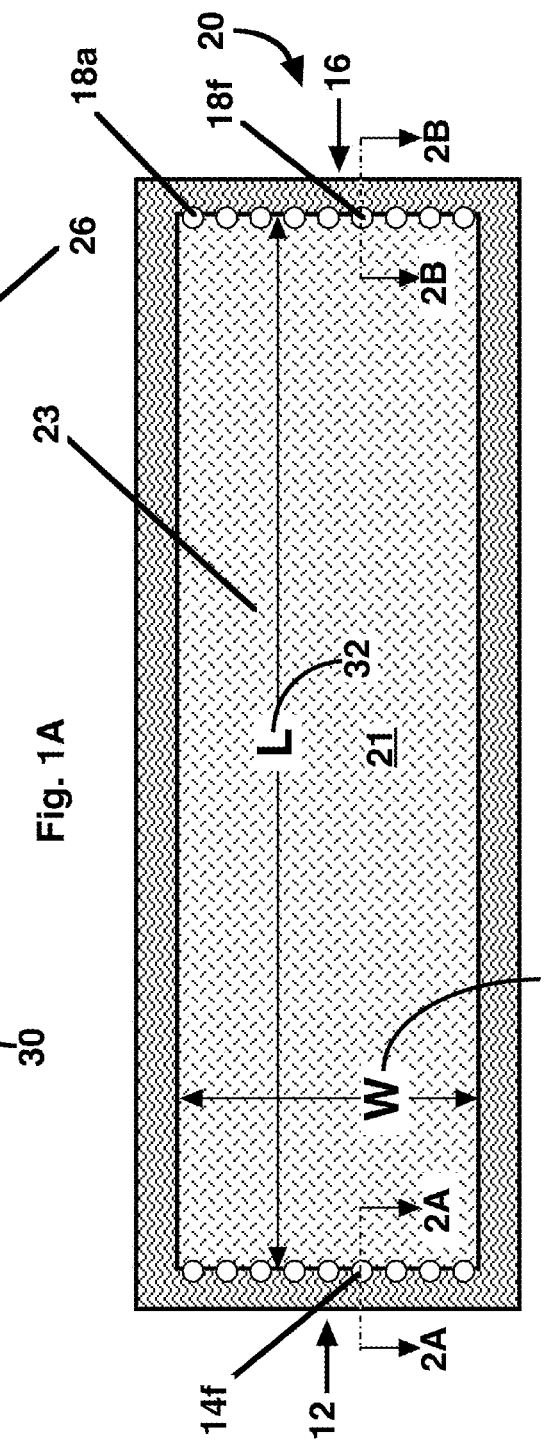
Fig. 1A
Fig. 1B

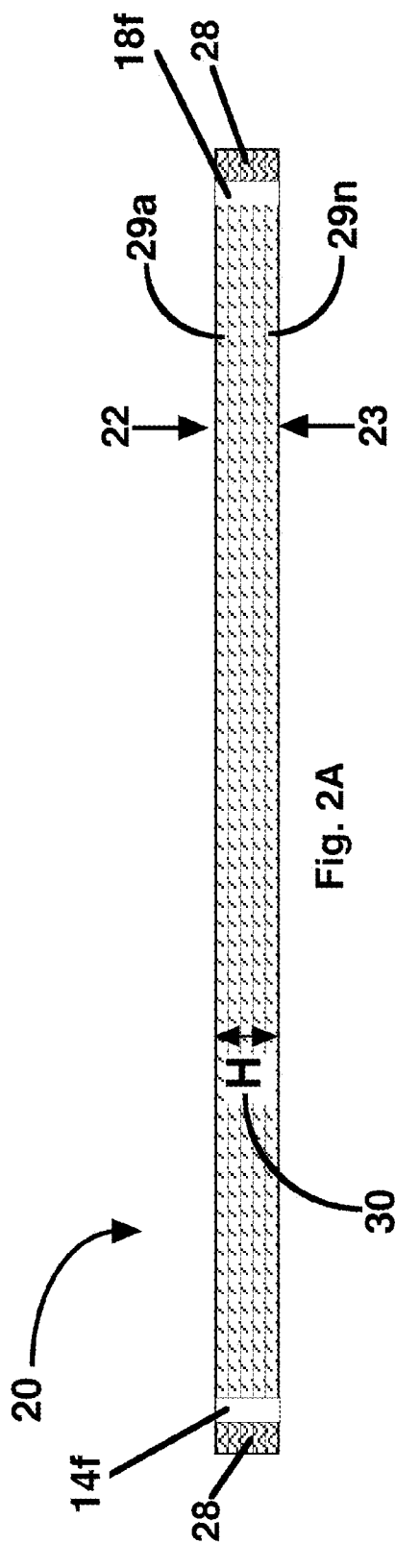
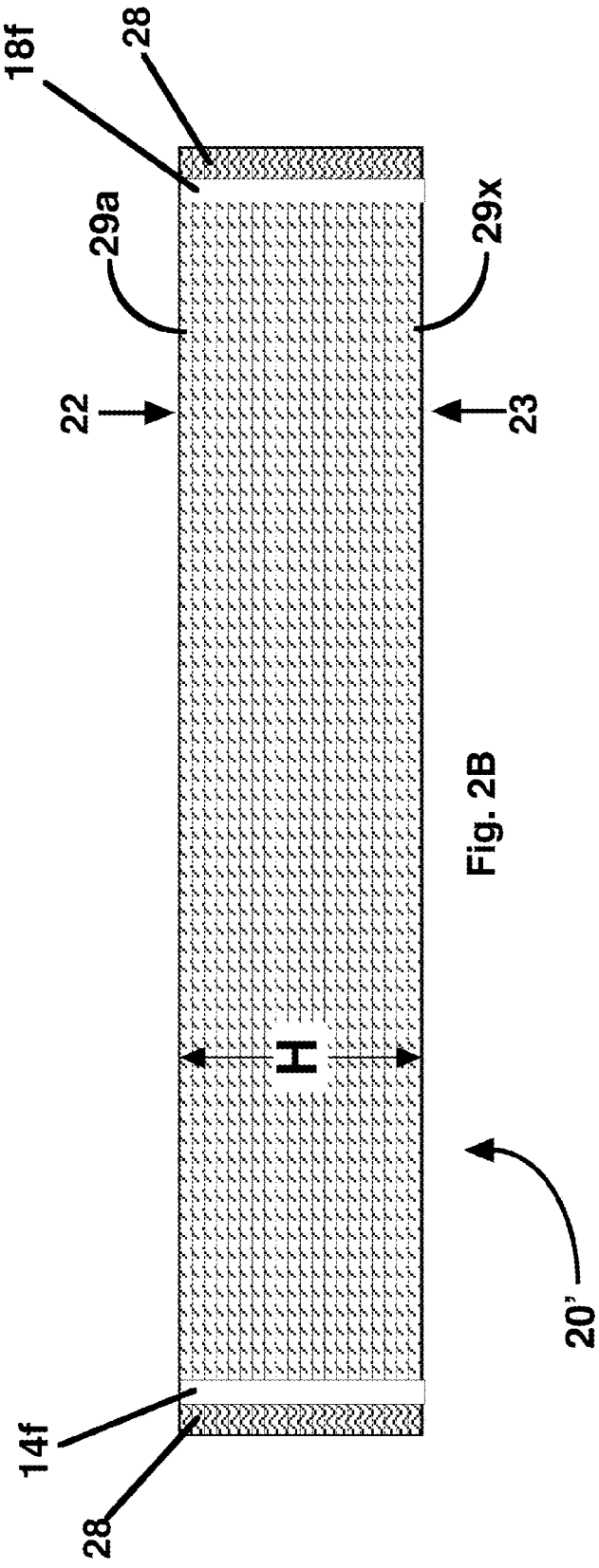

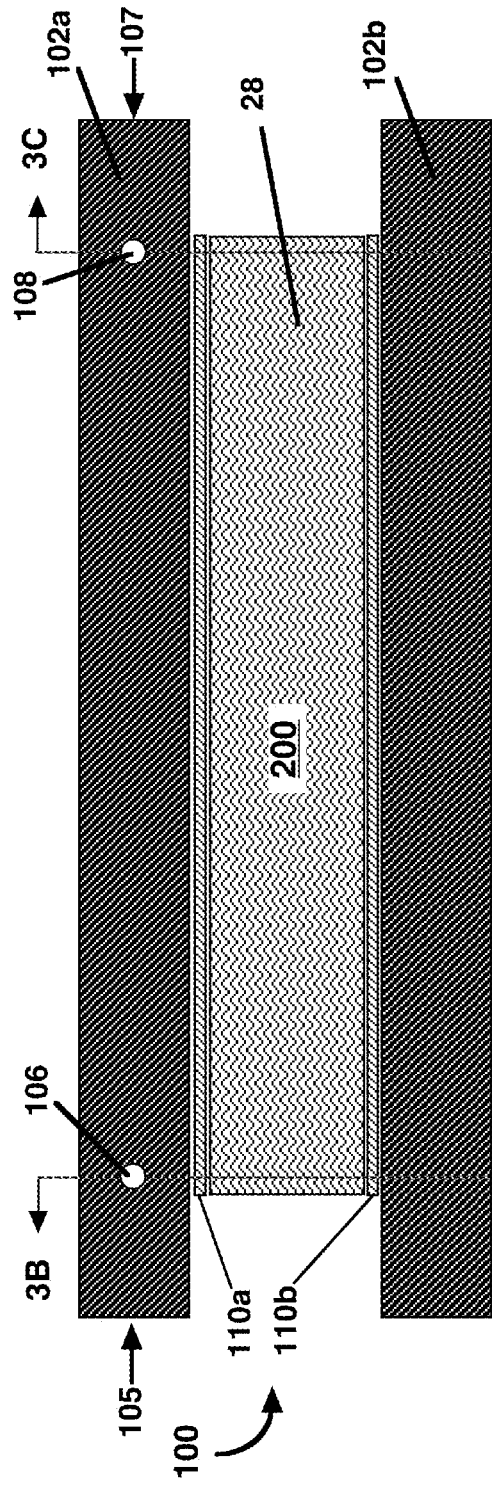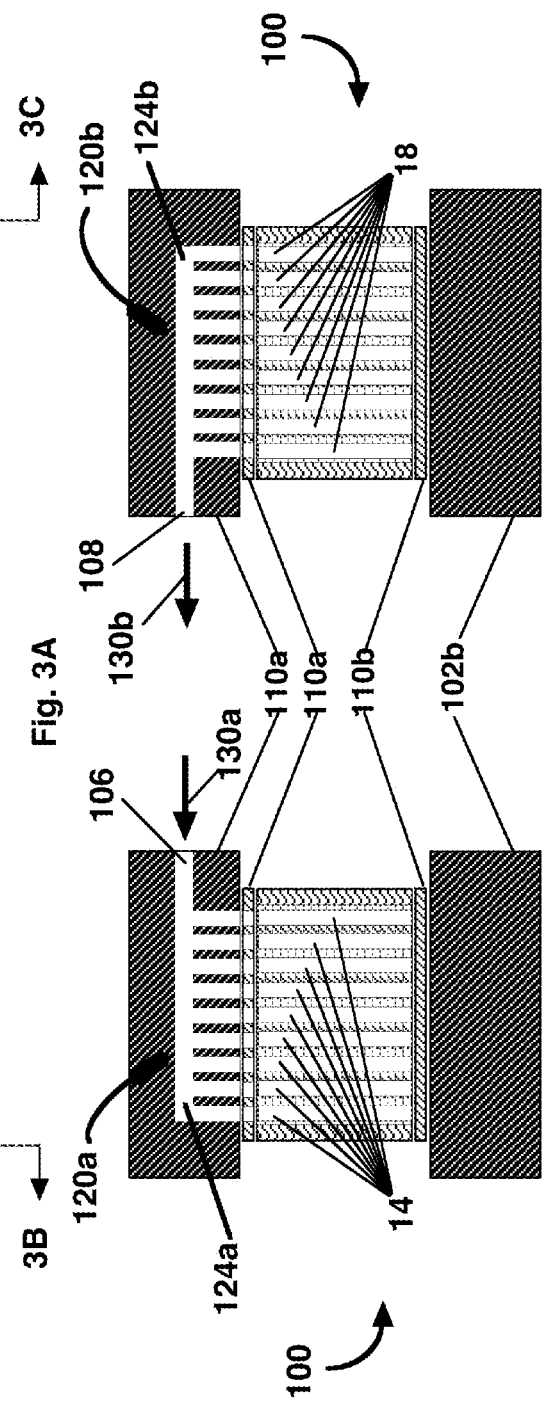
Fig. 3A
Fig. 3B
Fig. 3C

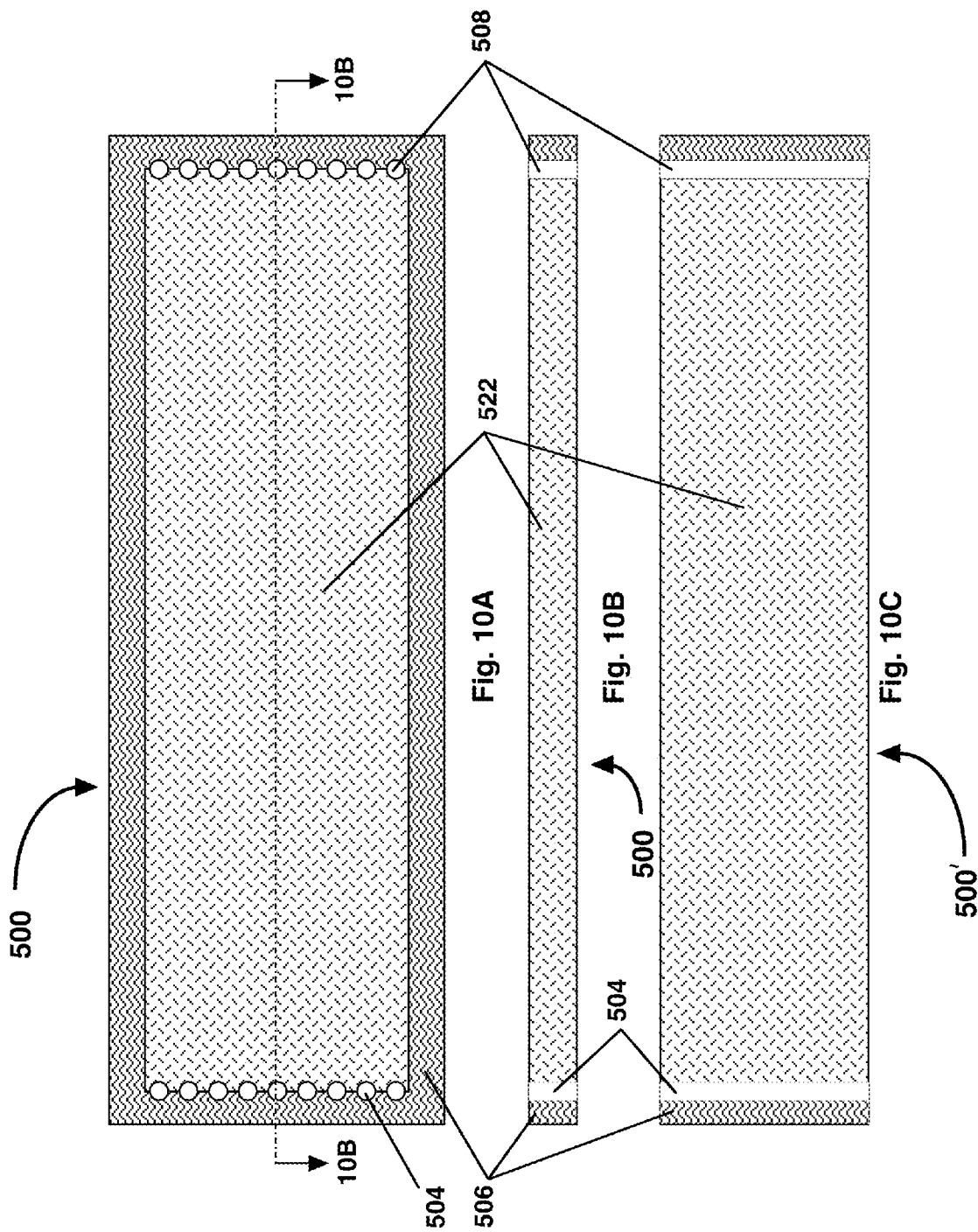

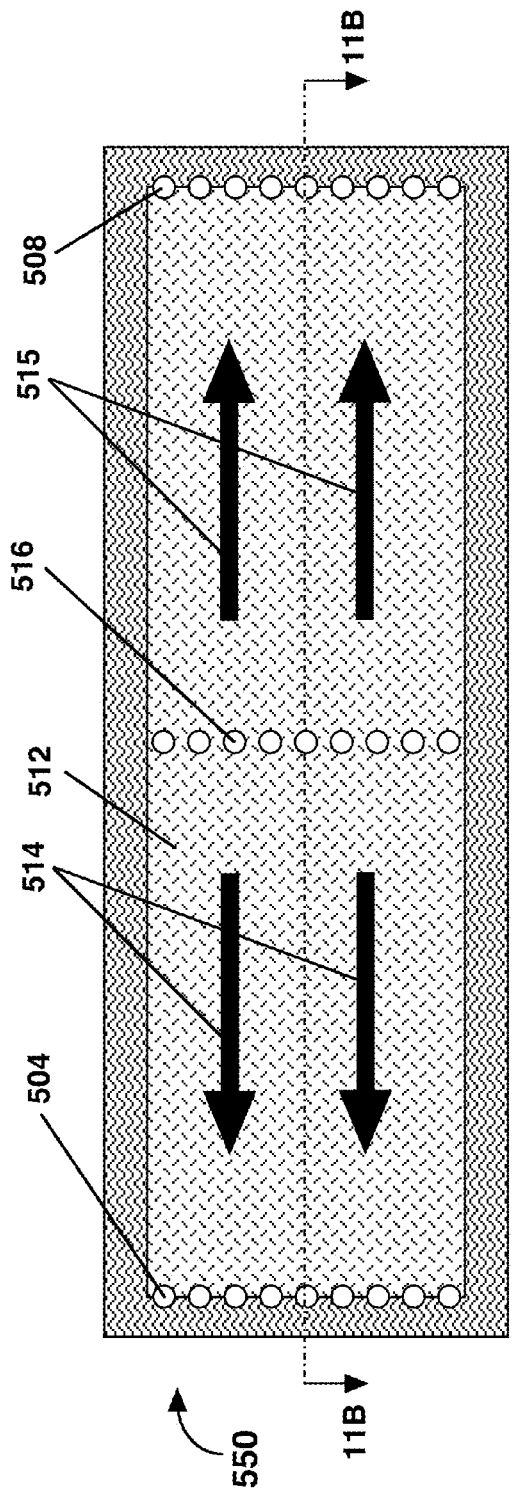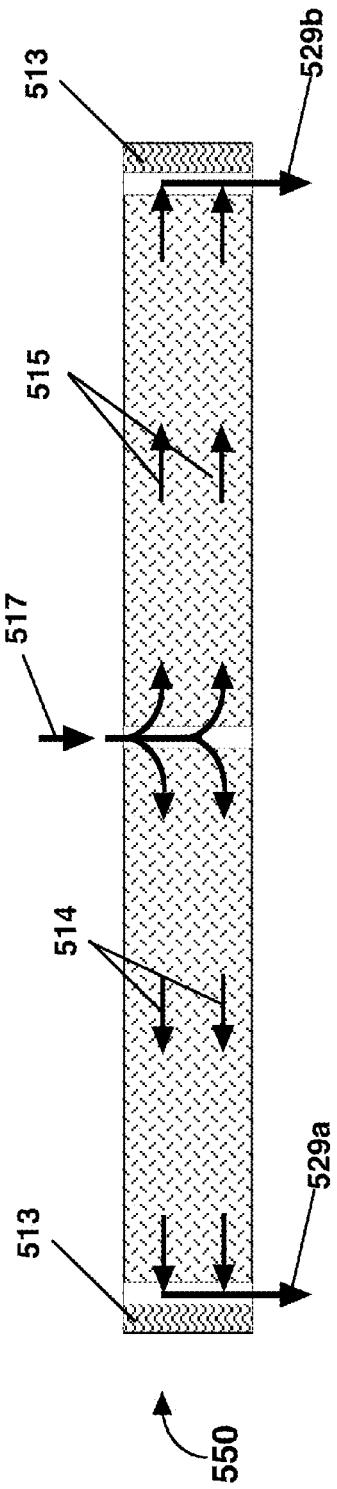

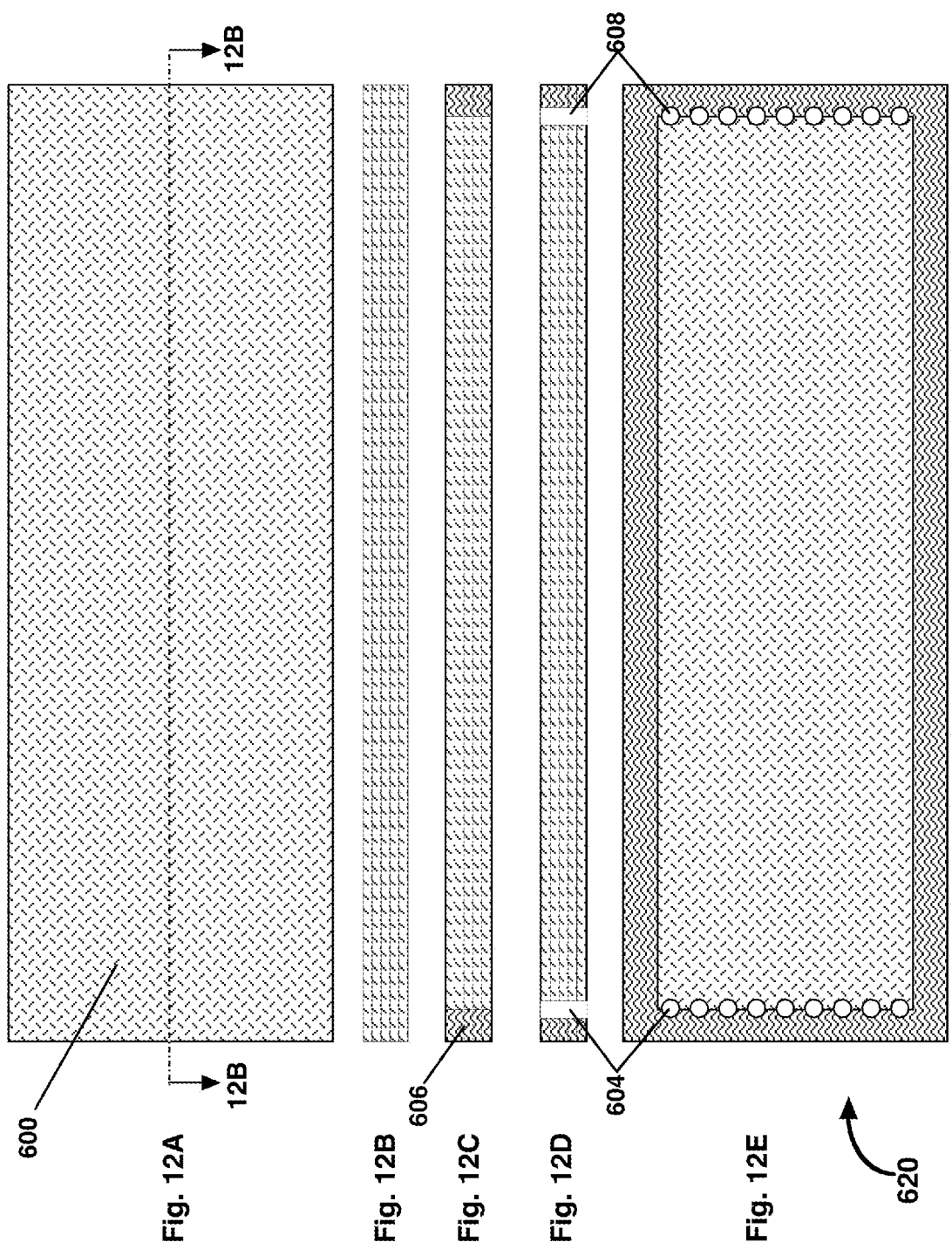

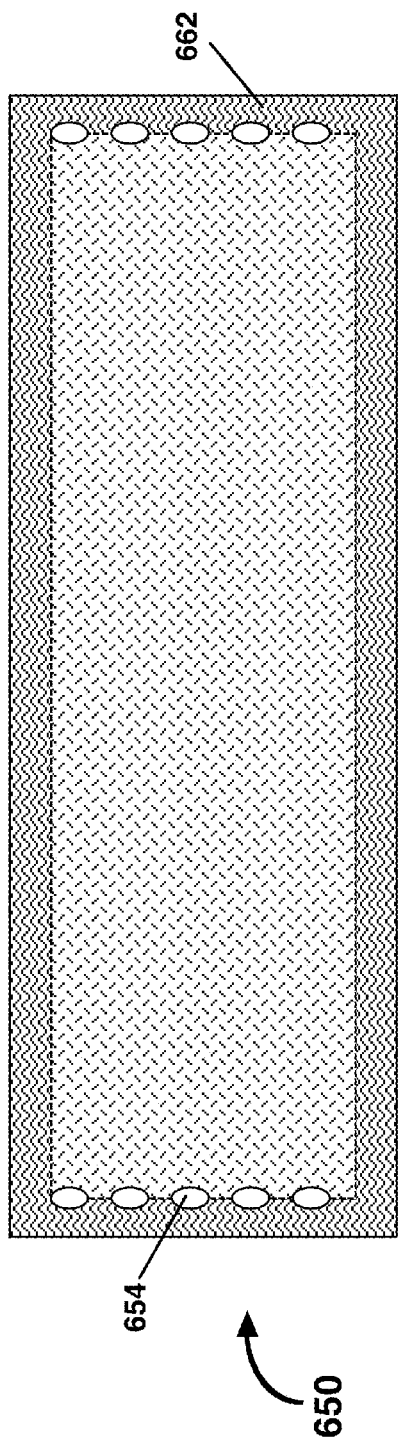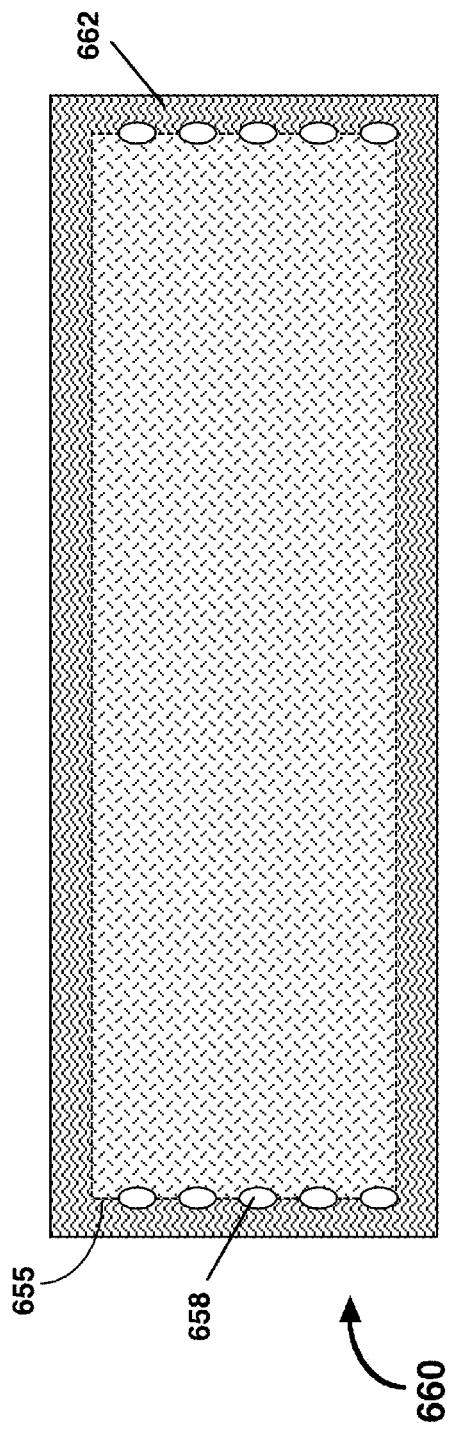

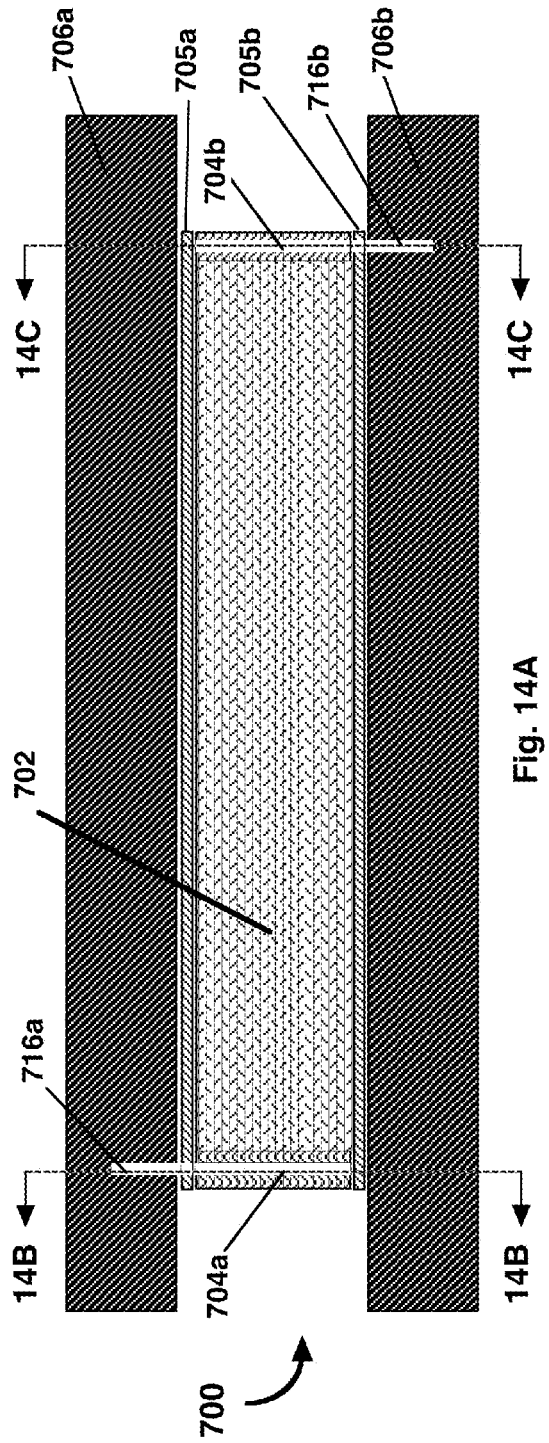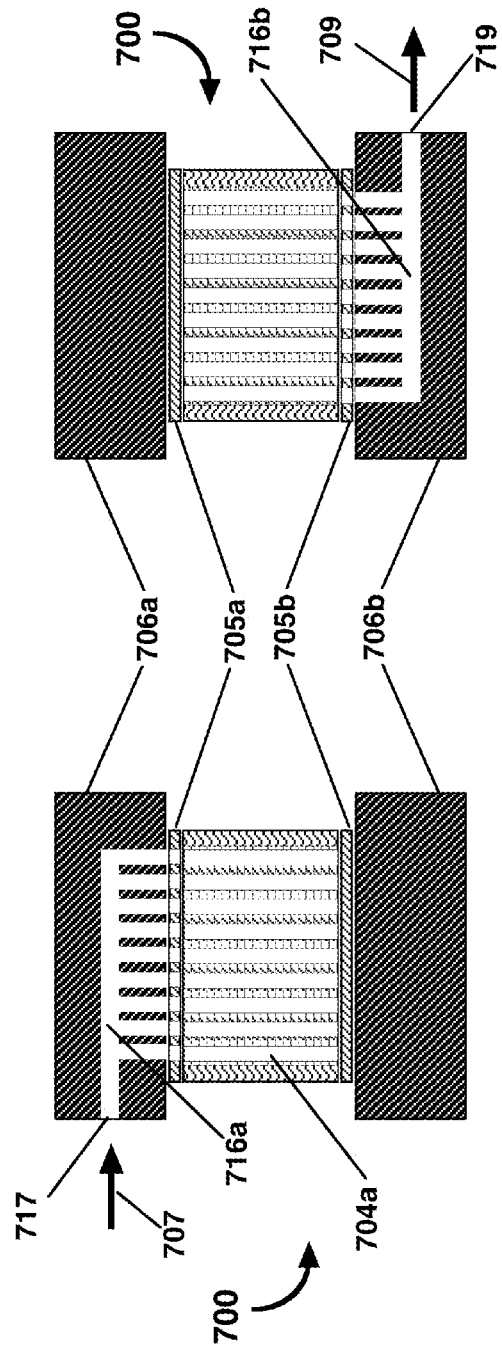

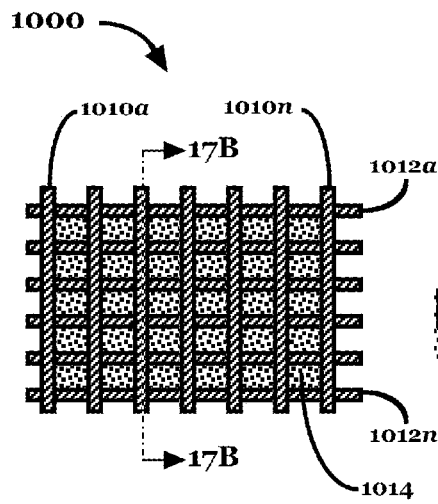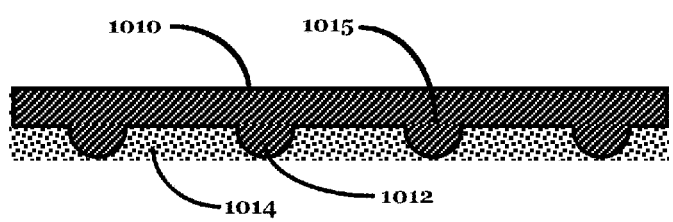
Fig. 17A  Fig. 17B
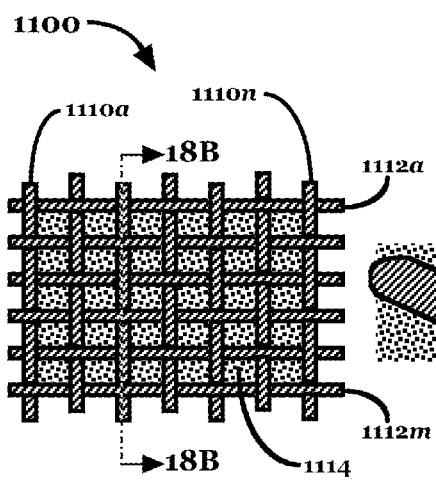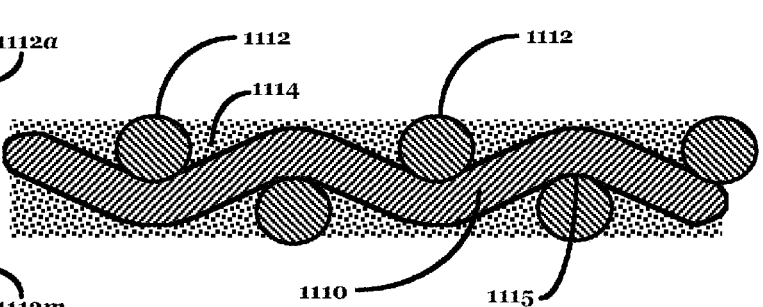
Fig. 18A  Fig. 18B

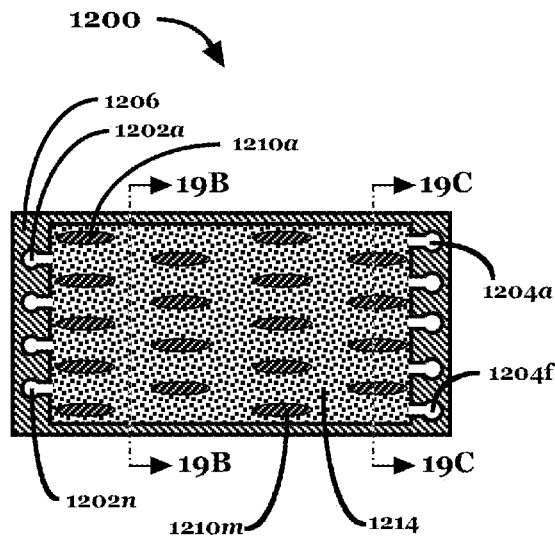
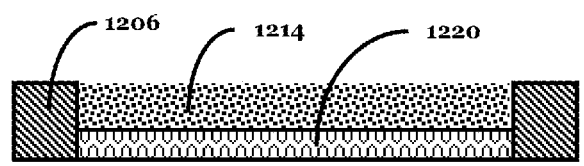
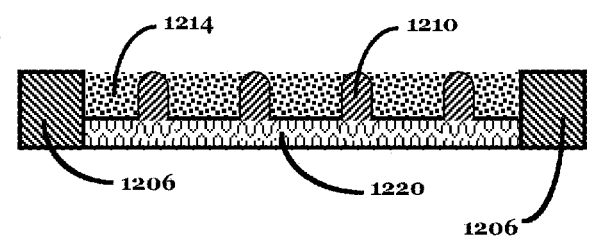
Fig. 19A  Fig. 19B  Fig. 19C
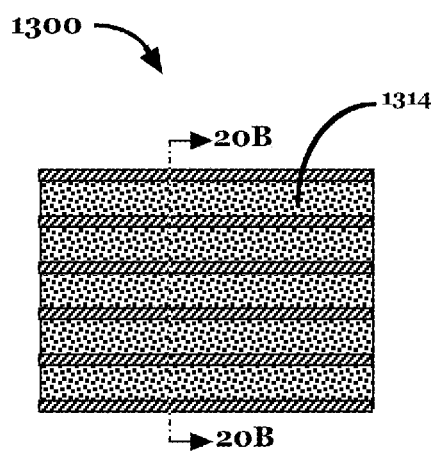
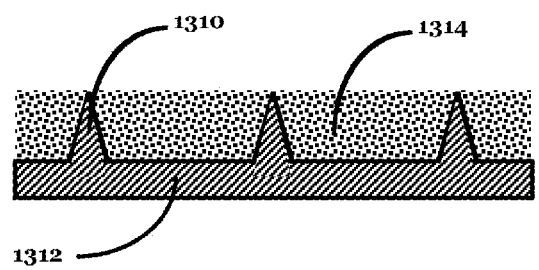
Fig. 20A  Fig. 20B

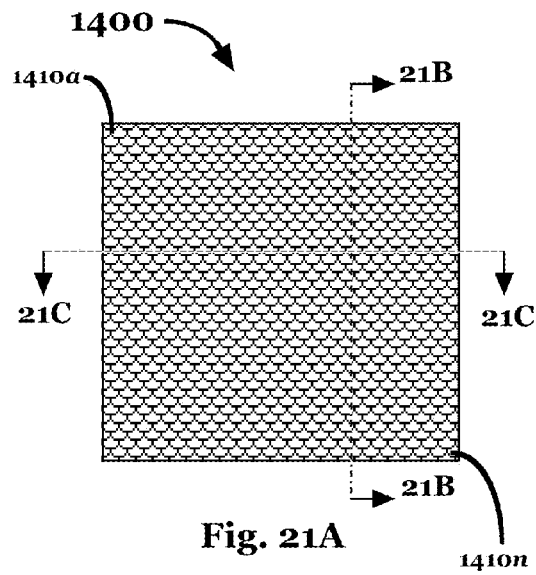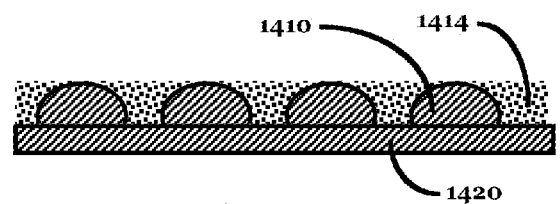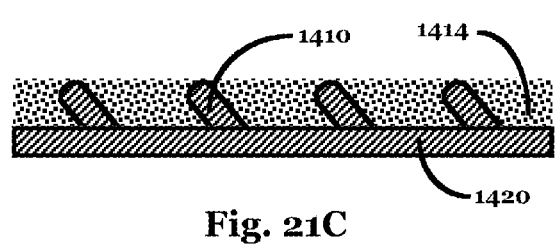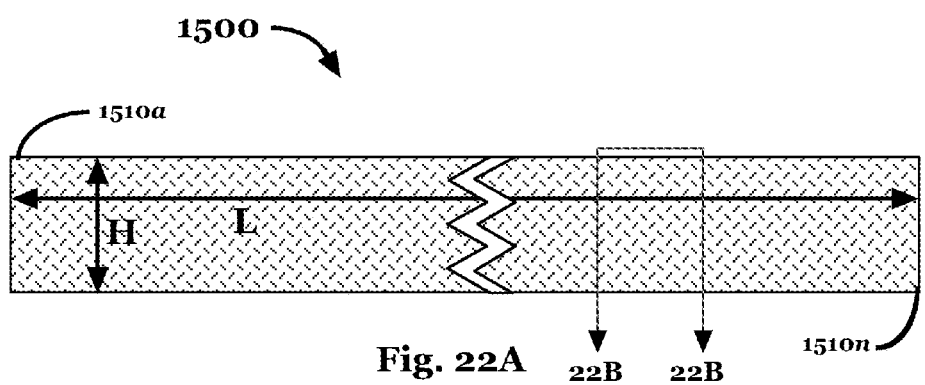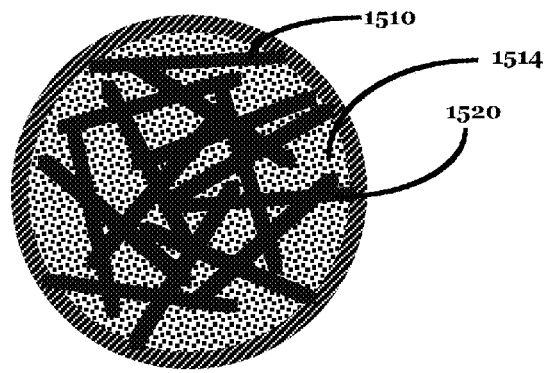

STACKABLE PLANAR ADSORPTIVE DEVICES

CROSS-REFERENCE TO RELATED APPLICATIONS

This application is a continuation in part of application Ser. No. 13/013,807, filed Jan. 25, 2011 which claims the benefit of U.S. Provisional Application No. 61/297,896, filed Jan. 25, 2010. These applications are incorporated by reference in their entireties.

TECHNICAL FIELD

The field of this invention is related to adsorptive devices and processes, of which chromatography is an example. More specifically, this invention relates to devices having rigid scaffolds packed with adsorptive beads to form an adsorptive bed.

BACKGROUND OF THE INVENTION

Adsorptive processes and devices are widely used in the analysis and purification of chemicals, including synthetic and naturally-derived pharmaceuticals, blood products and recombinant proteins.

Chromatography is a general separation technique that relies on the relative affinity or distribution of the molecules of interest between a stationary phase and a mobile phase for molecular separation. The stationary phase typically comprises a porous media imbibed with solvent. The mobile phase comprises a solvent, which can be aqueous or organic, that flows through the interstitial space that exists between the spaces occupied by the stationary phase.

Columns with associated end caps, fittings and tubing are the most common configuration, with the media packed into the tube or column. The mobile phase is pumped through the column. The sample is introduced at one end of the column, the feed end, and the various components interact with the stationary phase by any one of a multitude of adsorptive phenomena. The differential adsorptive interaction between the components and media leads them to traverse the column at different velocities, which results in a physical separation of the components in the mobile phase. The separated components are collected or detected at the other end of the column, the eluent end, in the order in which they travel in the mobile phase. In one type of adsorptive process, referred to as capture and release process, the process involves multiple steps, first to load the media, then to wash it, and then to elute it.

Chromatographic methods include among other methods, gel chromatography, ion exchange chromatography, hydrophobic interaction chromatography, reverse phase chromatography, affinity chromatography, immuno-adsorption chromatography, lectin affinity chromatography, ion affinity chromatography and other such well-known chromatographic methods.

Adsorptive media comes in many forms, most typically in the form of beads. The beads are conventionally packed into columns, with the column walls and ends immobilizing the beads into a fixed adsorptive bed, a bed being a porous 3 dimensional structure containing the stationary phase (in this case the beads) and the pore space through which the mobile phase flows/permeates (the space between the beads). Adsorptive media may also be formed into cohesive beds that retain their shape by virtue of the cohesion in the media; just like beds made with beads, these beds have two distinct regions, one occupied by the stationary phase and another occupied by the mobile phase; this type of media are referred to as monolithic media, or simply as monoliths. Media may also be formed in the shape of fabrics or webs, which can be stacked to form an adsorptive bed. Beds made of monoliths are cohesive in 3 dimensions, whereas beds made of webs are cohesive only in 2 dimensions; beds made of beads alone have no cohesion, requiring the column to maintain its shape.

Planar adsorptive processes and devices have been in use. Examples of planar adsorptive processes are paper chromatography and thin layer chromatography. In these processes, the adsorptive bed has a planar geometry in contrast to the cylindrical geometry of conventional chromatography beds. The mobile phase typically flows through the stationary phase by virtue of the capillarity of the porous medium, which draws the solvent into the porous space of the media. These processes do not require that the fluid pressure be contained since the fluid is not being pumped. More recently, a form of planar chromatography has been developed in which the fluid is pumped; this process is referred to as over-pressure planar chromatography (OPPC). OPPC requires that the media be contained in apparatus that maintains the shape of the bed in spite of the pressures used. In all cases, the planar adsorptive beds used in these processes are very thin, usually no thicker than a millimeter, making them suitable for analytical applications.

Membrane-based adsorptive devices have been developed. In these devices the adsorptive media is either supported by or embedded into a flat micro-porous membrane, which is then fabricated into filtration devices. Two or more of these membranes may be stacked to form an adsorptive bed with a longer flow path; however, the number of layers that can be stacked is limited by the low hydraulic permeability of microfiltration membranes. Such filtration devices are characterized by the fact that the fluid being treated flows through the adsorptive media in a direction substantially perpendicular to the planar dimension of the media. The virtue of membrane adsorbers is their fast kinetics, enabling them to have short bed depths and high feed rates. However, the same attributes that confer them with fast kinetics severely and limit their capacity. Additionally, the intrinsic geometry of existing membrane adsorbers limit their scalability, the largest ones typically being no larger than 5 liters.

Furthermore, the bed depth, or absorptive path length, important in purification steps requiring resolution, is limited in membrane-based devices due to the low hydraulic permeability of microporous membranes. Membrane absorptive media is expensive, because the high cost of the membrane substrate and the challenges of functionalizing the membrane surface with absorptive chemistry. Finally, membrane-based adsorptive devices inherently have low capacity, as a result membrane adsorption devices have found applicability primarily in "polishing" steps—e.g. virus and DNA removal—where the adsorptive load is negligible, rather than in the core capture/purification steps.

Conventional chromatographic devices require that beads must be packed into a column. The quality of this packing determines the performance of the adsorbing bed. This adds another source of variability to the chromatographic process and must be validated before use. Furthermore, beds packed with beads are prone to voiding, a phenomenon whereby the beads settle into a denser structure resulting in the creation of voids and in non-homogeneities in the packing density of the bed, all of which results in a deterioration of performance. This is especially true in columns packed with soft beads.

SUMMARY

The special demands imposed on pharmaceutical manufacturing processes make it highly desirable that such processes be easily scaled-up. In particular, there are many advantages to processes that can be scaled-up without having to reset or redevelop the processing conditions. Such processes are referred to in the industry as linearly-scalable processes; in essence, the parameters that define the separation process and operating conditions remain unchanged as the process moves from the laboratory bench (i.e., discovery), where the column can be as small as several milliliters, to the process development laboratory (e.g., columns of several liters), to clinical manufacturing, to large-scale manufacturing, where the chromatography column can be as large as several hundred liters. Existing chromatographic devices are not linearly scalable, their design and geometry requiring significant alterations as the device size increases, thereby introducing uncertainties and unwanted risks as processes evolve from drug discovery, to clinical trials, to small-scale and then to large-scale manufacturing.

An adsorptive bed to receive a liquid flow, according to one embodiment, includes a housing having a first surface, a scaffold disposed within the housing in contact with the first surface. The scaffold includes a stress absorbing substantially rigid structure and a plurality of open cells disposed within the rigid structure. The adsorptive bed further includes a plurality of adsorptive beads filling the plurality of open cells forming a packed bed of the plurality of adsorptive beads and the scaffold restricts movement of the plurality of adsorptive beads, absorbs compressive stress induced by a hydraulic pressure gradient along a direction of the liquid flow and transfers a portion of the induced compressive stress to the first surface of the housing. Such a device enables the use of adsorptive bead-based media in planarly cohesive adsorptive beds. Such a device can be linearly scaled to operate from the process development laboratory scale, to clinical manufacturing, to large-scale manufacturing.

Aspects of the present invention relate to absorptive devices that have the high capacity of beads but the operational advantages of webs, and in particular webs that have the properties of native agarose in rigid form. Other aspects of the present invention relate to linearly scalable devices and absorptive devices that provide the flexibility to develop new purification processes beyond the conventional batch chromatography processes.

A chromatographic method to process a liquid includes providing an adsorptive bed comprising as described above, processing the liquid using a rapid cycling controller and operating at a pressure of greater than 100 psi. A chromatography system includes devices using the adsorptive bed described above and additionally include at least one pump and at least one valve controlling a liquid feed stream and a rapid cycling controller coupled to the at least one pump and at least one valve. Such a technique and corresponding system allows operation of adsorptive bed packed in a chromatography column or an adsorptive bed is sealed in a monolithic block to operate at higher flow rates and pressures than can be achieved with conventional devices.

BRIEF DESCRIPTION OF DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings. The following drawings are illustrative of embodiments of the invention and are not meant to limit the scope of the invention as encompassed by the claims.

FIG. 1A is a schematic diagram of a perspective top view of an adsorptive device according to an aspect of the invention;

FIG. 1B is a schematic diagram of a bottom view of the adsorptive device of FIG. 1;

FIGS. 2A and 2B are schematic diagrams of cross sectional views (along section 2A-2A) of the device of FIG. 1A;

FIG. 3A is a schematic diagram of a side view of an adsorptive device for processing a fluid according to an aspect of the invention;

FIGS. 3B and 3C are schematic diagrams of cross sectional views (along section 3B-3B and along section 3C-3C) of the device of FIG. 2A showing details of the end plates and manifolds;

FIGS. 7A, 7B, 8, 9, 10A, 10B, 10C, 11A and 11B, are schematic diagrams showing alternative geometries, media types and flow profiles of cassettes according to other aspects of the invention;

FIGS. 12A, 12B, 12C, 12D, 12E, 13A and 13B are schematic diagrams showing alternative fabrication methods of devices according to the invention;

FIGS. 14A, 14B and 14C are schematic diagrams showing a cassette assembly according to an aspect of the invention;

FIG. 17A is a schematic diagram showing a planarly cohesive separator sheet based on a bi-planar plastic netting suitable for supporting adsorptive beads according to aspects of the invention;

FIG. 17B is a cross section view of the planarly cohesive separator sheet taken along section 17B-17B of FIG. 17A;

FIG. 18A is a schematic diagram showing a planarly cohesive separator sheet based on a woven screen with a square weave according to aspects of the invention;

FIG. 18B is a cross section view of the planarly cohesive separator sheet taken along section 18B-18B of FIG. 18A;

FIG. 19A is a schematic diagram showing a planarly cohesive separator sheet based on a molded plate according to aspects of the invention;

FIG. 19B is a cross section view of the planarly cohesive separator sheet taken along section 19B-19B of FIG. 19A;

FIG. 19C is a cross section view of the planarly cohesive separator sheet taken along section 19C-19C of FIG. 19A;

FIG. 20A is a schematic diagram showing a planarly cohesive separator sheet based on an extruded sheet according to aspects of the invention;

FIG. 20B is a cross section view of the planarly cohesive separator sheet taken along section 20B-20B of FIG. 20A;

FIG. 21A is a schematic diagram showing a planarly cohesive separator sheet based on a perforated plate or sheet according to aspects of the invention;

FIG. 21B is a cross section view of the planarly cohesive separator sheet taken along section 21B-21B of FIG. 21A;

FIG. 21C is a cross section view of the planarly cohesive separator sheet taken along section 21C-21C of FIG. 21A;

FIG. 22A is a schematic diagram showing a planarly cohesive separator sheet based on a sintered sheet of randomly packed rods or fibers according to aspects of the invention;

FIG. 22B is a cross section view of the planarly cohesive separator sheet taken along section 22B-22B of FIG. 22A;

DETAILED DESCRIPTION OF THE INVENTION

Figure 4:
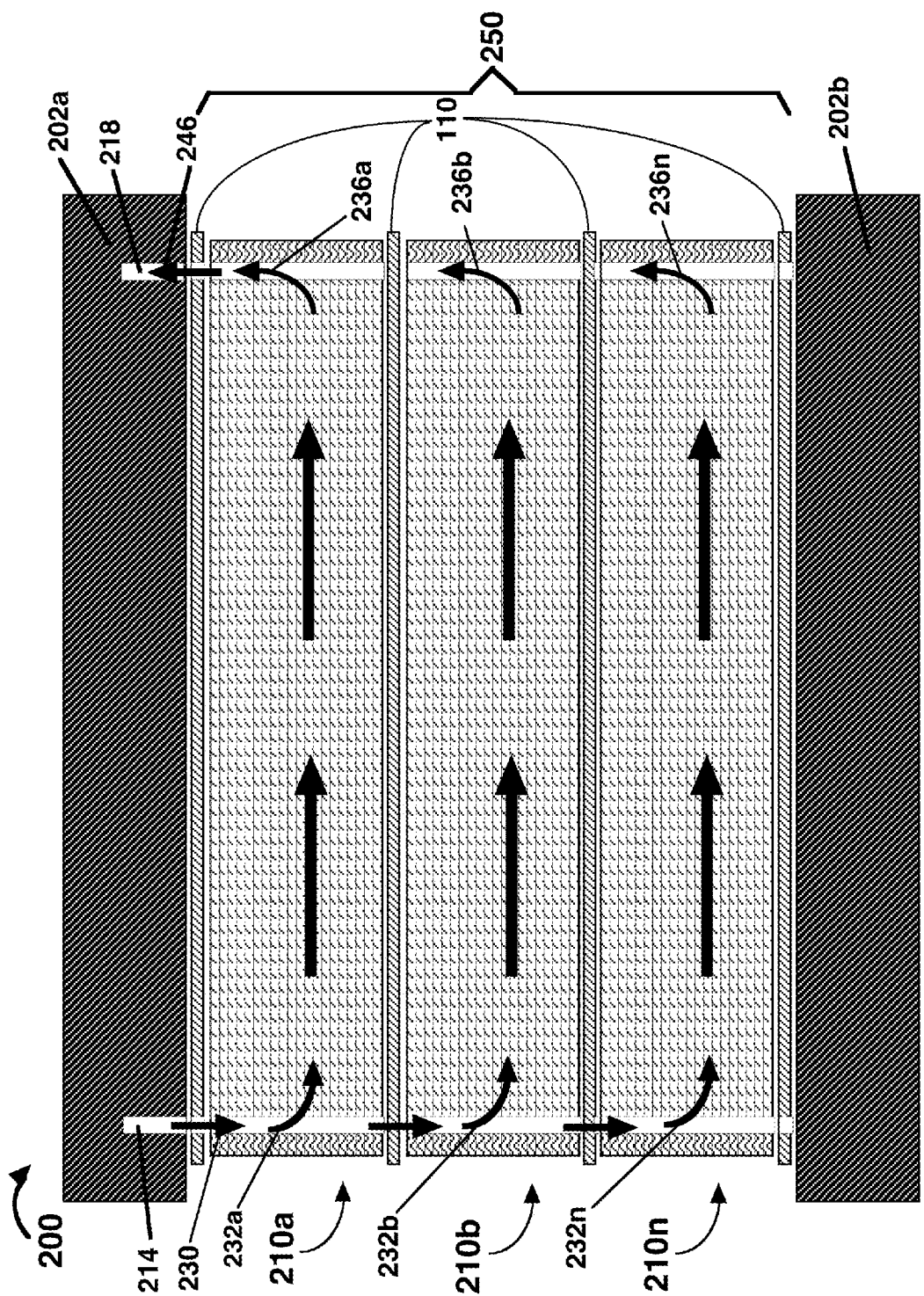
FIG. 4 is an elevation view of a stack of cassettes hydraulically in parallel forming a composite cassette.

This invention generally relates to devices and processes suitable for preparative and manufacturing processes, and more specifically to processes used in the manufacture in the pharmaceutical industry for the production of medicinal or therapeutic products.

In contrast to conventional devices, applicants have discovered a way to support adsorptive media in a configuration that is linearly scalable and self supporting. Embodiments of the invention utilize planarly cohesive media. A web of adsorptive media, as for example, Macro-IPN media, is planarly cohesive. The media retains its shape even when pulled apart by a tensile force. A monolith is also planarly cohesive, except that it is much thicker than a web. The cohesion plane of planarly cohesive media is oriented in parallel to the planar surfaces of the adsorptive device. The cohesiveness of the media along the cohesion plane enables the fabrication of adsorptive media blocks as described below.

The term adsorptive media, chromatography media, and media are herein used interchangeably to refer to the stationary phase of an adsorptive device; media can also refer a single type of medium. As used herein, intimate contact generally refers to the scale of the void space left between adjacent layers, and means that these void spaces are of the same order of magnitude as the scale of the interstitial space occupied by the mobile phase within the beds. The term solvent and mobile phase are used herein interchangeably to refer to the stationary phase. The term lateral flow means fluid flow within the media along the cohesion plane; for example, in web-based adsorptive media lateral flow means flow along the plane of the web, in contrast to flow that is perpendicular to the plane of the web. The term adsorptive block and adsorptive device and cassette are used interchangeably to refer to the planarly cohesive beds of adsorptive media used in devices disclosed herein. The term isotropic means that the porous media through which the fluid flows has a homogenous porous structure perpendicular to the direction of flow, such that the specific resistance to flow is independent of the location of the in the media in planes perpendicular to the direction of flow; the importance of isotropic media is elaborated upon further below. By substantially it is meant that the deviations of the values of the property being described are sufficiently small to enable the adsorptive device to perform as expected.

Referring to FIGS. 1A-1B, an adsorptive device 10 includes at least one block 20 comprising planarly cohesive, substantially isotropic adsorptive media 21, the block has a first end 12, a second end 16, a first substantially planar surface 22, a second substantially planar surface 23, at least one sidewall 26 substantially perpendicular to the first and second planar surfaces 22, 23. The block further comprises a first plurality of distribution passageways 14a-14n (collectively referred to as distribution passageway 14) disposed within the at least one block 20, adjacent the first end 12 and substantially perpendicular to the first and second planar surfaces 22 and 23, a second plurality of distribution passageways 18a-18n (collectively referred to as distribution passageway 18) disposed within the at least one block 20 adjacent the second end and substantially perpendicular to the first and second planar surfaces 22 and 23, and a peripheral edge seal 28 encapsulating the at least one sidewall 26 having a planar surface portion 24.

The alignment and location of the distribution passageways 14 and 18 with respect to each other and the geometrical shape of the first and second planar surfaces 22 and 23 (also referred to as the footprint) are designed to induce substantially uniform lateral flow of fluid within the block 20 from the first end 12 to the second end 16. The block 20 may have a variety of footprints, for example, rectangular, circular, trapezoidal, etc. The shape of the footprint in conjunction with the location of the distribution passageways 14 and 18 are the design factors responsible for inducing the desired uniform flow.

The block 20 is a three-dimensional device characterized by a length 32, a height 30 and a width 34. The direction of fluid flow is aligned with the length coordinate; the width of the planar surfaces 22 and 23 defines the width 34 and the height 30 of the block 20 is the dimension perpendicular to the planar surfaces 22 and 23.

In operation, fluid is introduced and distributed into distribution passageways 14 and collected and removed from distribution passageways 18. The adsorptive device 10 is rendered "self-supporting" by the encapsulation of the sidewall 26 defined by the cohesion planes, parallel to the planar surfaces 23 and 23, of the planarly cohesive, substantially isotropic adsorptive media 21. The blocks 20 of adsorptive device 10 do not require additional support structures to contain the hydraulic pressures generated in use, enabling the blocks 20 to be easily loaded and unloaded between end plates shown below in conjunction with FIG. 2A. This attribute additionally allows the stacking of blocks 20 without a change of the end plates enabling very easy scale-up.

It is understood that in an adsorptive device 10 there are numerous possible paths, or streamlines, between the distribution passageways 14 and 18. The fluid in each streamline takes a certain amount of time to complete the trajectory from the first end 12 to the second end 16, this time being typically referred to as the residence time. High performance adsorptive devices require that the variation in the residence time of all the streamlines be as small as possible. To achieve this performance attribute, adsorptive blocks should have adsorptive media that is substantially isotropic along planes perpendicular to the direction of flow, in addition to having streamlines that have substantially uniform length. Flow uniformity is the net result of this combination of properties.

In one embodiment the layers of adsorptive media are formed from web-based adsorption media, for example, macroporous IPN media produced in a web and cut to fit the block 20. Macroporous IPN media is described in PCT application PCT/US2010/024804 entitled POROUS INTERPENETRATING POLYMER NETWORKS WITH IMPROVED PROPERTIES, filed Feb. 19, 2010, which is incorporated by reference in its entirety. In other embodiments the layers of adsorptive media might comprise Empore discs (3M Corp., St. Paul, Minn.), or Whatman Chromatography Paper (GE Life Sciences, Westborough Mass.).

FIG. 2A shows a magnified section view (through Section 2A-Section 2A of FIG. 1A) of distribution passageways 14 on the first end of block 20. FIG. 2A shows a cross section of block 20 having four layers of web 29. FIG. 2B shows a block 20' having more layers of web 29 and therefore a higher height than the block 20 shown in FIG. 1A. Block 20 can include multiple web layers 29a-29n (collectively referred to as web layer 29) of the planarly cohesive, substantially isotropic adsorptive media 21.

The feed stream (not shown) is distributed along the width of the block 20 by manifold 120 (shown below in conjunction with FIG. 3B) entering each one of several passageways 14a-14n as a feed sub-stream, which is further distributed and turned forming lateral flow streams within each web layer 29. In contrast to filtration devices, lateral streams 8 flow along the plane that defines web layer 29 (i.e., these flow laterally rather than perpendicularly to the plane of web layer 29).

FIG. 2B shows adsorptive device 10' which includes additional web layers 29 as compared to adsorptive device 10 of FIG. 2A.

Now referring to FIGS. 3A-3C, an adsorptive device 100 for processing a fluid includes a pair of end plates 102a and 102b (also referred to as end plate 102). Each end plate 102 has a feed end 105 and an eluent end 107. At least one of the pair of end plates 102 has a feed inlet 106 disposed at the feed end 105, and at least one of the pair of end plates 102 has an eluent outlet 108 disposed at the eluent end 107. The adsorptive device 100 further includes a plurality of cassettes 200 in a stacked configuration (shown here as a single cassette 200, stacked configurations described below in conjunction with FIGS. 3, 4 and 5).

Each cassette 200 is similar to the block 20 of FIG. 1A. As described above, the cassette 200 geometry and location of the passageways induce substantially uniform lateral flow from the feed end 105 to the eluent end 107 within the block, the uniform lateral flow being parallel to the first and second substantially planar surface. Here, one of the pair of end plates 102a is adjacent to the first surface 22 of the cassette 200 and a second one of the pair of end plates 102b is adjacent to a second surface 23 of the cassette 200.

Still referring to FIGS. 3A-3C, cassette 200 further comprises peripheral edge seal 28 forming an impermeable seal of web 29 (also called "seal" and "peripheral edge seal") using a sealant. In one embodiment a thermoset resin is used and in another embodiment a thermoplastic resin is used to form the seal. Other sealants known in the art can also be used. Peripheral edge seal 28 is adhered to web 29 forming a structural boundary to include the elevated pressures present inside the cassette. Cassette 200 further comprises passageways 14 and 18 distributed along its width at both the feed and eluent ends, respectively, and are used for the introduction of the feed stream and collection of the eluent stream along the width of cassette 200. Passageways 14 (also referred to as distribution passageways) penetrate cassette 200 along its height from top to bottom, enabling the distribution of fluid along the height H.

FIG. 3B shows a sectional side view of a manifold 120a disposed in end plate 102a. Manifold 120a is used to introduce the feed stream 130a, whereas manifold 120b disposed on the opposite end of end plate 102a is used to recover the eluent stream 130b, as shown in FIG. 3C. Flow passages 124a inside manifold 120a are used to distribute the feed stream to distribution passageways 14 in cassette 200. Flow passages 124b inside manifold 120b are used to collect the eluent stream from distribution passageways 18 in cassette 200. It is understood that there are several different operational configurations of the manifold 120a and 120b in the end plates 102a and 102b.

In certain embodiments, cassettes 210a-210n are stacked such that they are hydraulically in parallel as shown in FIG. 4 (hereafter referred to as a "parallel configuration"). In this case cassettes 210 form a composite cassette 250 whose height is equal to the sum of the heights of each cassette 210. Manifolds 120a and 120b (FIG. 3A) are used to support stacked cassettes 210 by means of support structure (not shown), which can be made of tie rods or of some sort of external press), and include passageways (not shown) to distribute the feed stream into the distribution passageways on the feed end and to collect the eluent stream from the eluent end of cassettes 210. Manifolds 120 are have a feed and an eluent end to match the feed and eluent ends of cassettes 210.

Feed and eluent distribution passageways 14 and 18 can be configured in several positions in the end plates. Both can be located only in the top manifold, or only in the bottom manifold. Alternatively, feed distribution passageways can be located only on the top end plate with eluent distribution passageways only on the bottom end plate or any combinations thereof, as long as there is at least one set of feed distribution passageways and one set eluent distribution passageways in either the top or bottom manifolds disposed within the end plates. Gaskets 110 may be used to obtain a reliable seal between adjacent cassettes 210 and between cassettes 210 and manifolds. Gaskets 110 may be integrated (and adhered) into each cassette 210, or may be a separate component that is added as part of a stack of cassettes 210 to form a block. To enable cassettes 210 to be stacked in the fashion shown in FIG. 4, these must be approximately of the same length and width, and the distribution passageways need to be similarly located so that they line up and are in fluid communication; however, it should be understood that while FIG. 4 shows cassettes 210 of the same height, cassettes can be of different heights.

Figure 5:
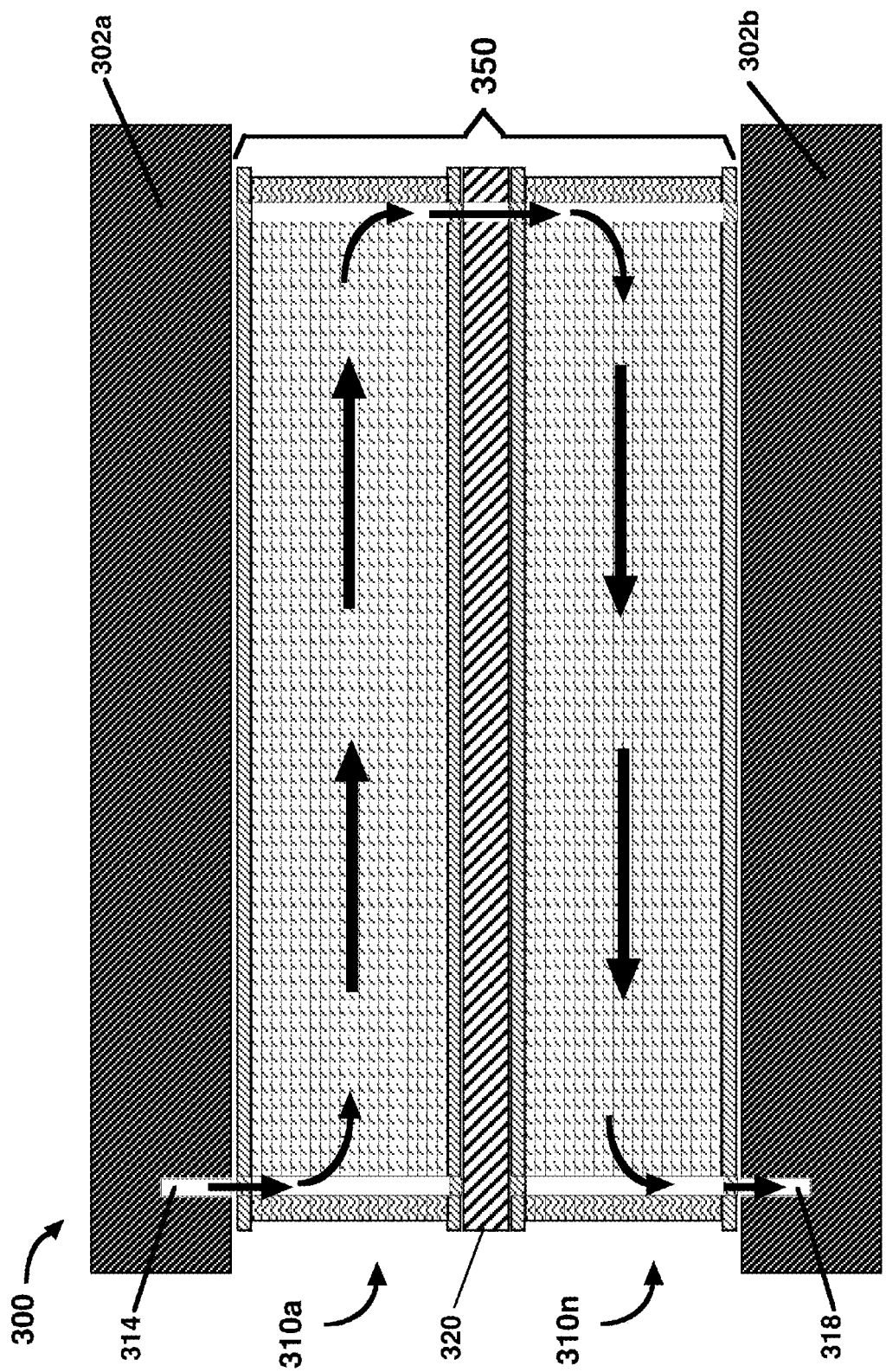
FIG. 5 is an elevation view of a stack of cassettes hydraulically in series forming a composite cassette.

Alternatively in other embodiments, cassettes are stacked such that they are hydraulically in series as shown in FIG. 5. In this case cassettes 310a-310n form a composite cassette 350 whose hydraulic length is equal to the sum of the lengths of each cassette 310 by virtue of flow diverter plate 320. Manifolds (not shown) are used to support stacked cassettes 310 by means of support structure (not shown), and include distribution to distribute the feed stream into the distribution passageways 314 on the feed end and to collect the eluent stream from the eluent end of cassettes 310. End plates have a feed and an eluent end to match the feed and eluent ends of cassettes 310. In contrast to the parallel configuration shown in FIG. 4, feed and eluent passageways must be located in separate manifolds. Gaskets 110 may be used to obtain a reliable seal between adjacent cassettes 310, between cassettes 310 and flow diverter plates 320, and between cassettes 310 and end plates. Gaskets 110 may be integrated (and adhered) into each cassette 310, or may be a separate component that is added as part of a stack of cassettes to form a block. To enable cassettes 310 to be stacked in the fashion shown in FIG. 5, these must be approximately of the same length and width, and the distribution passageways need to be similarly located so that they line up and are in fluid communication. However, it should be understood that while FIG. 5 shows cassettes 310 of the same height, cassettes can be of different heights; furthermore, two or more cassettes can be placed in series.

It is understood that it is possible to create composite cassettes utilizing combinations of parallel and series configurations as shown in FIGS. 4 and 5 by introducing flow diverter plates 320 at desired locations within a stack of cassettes 310.

Figure 6:
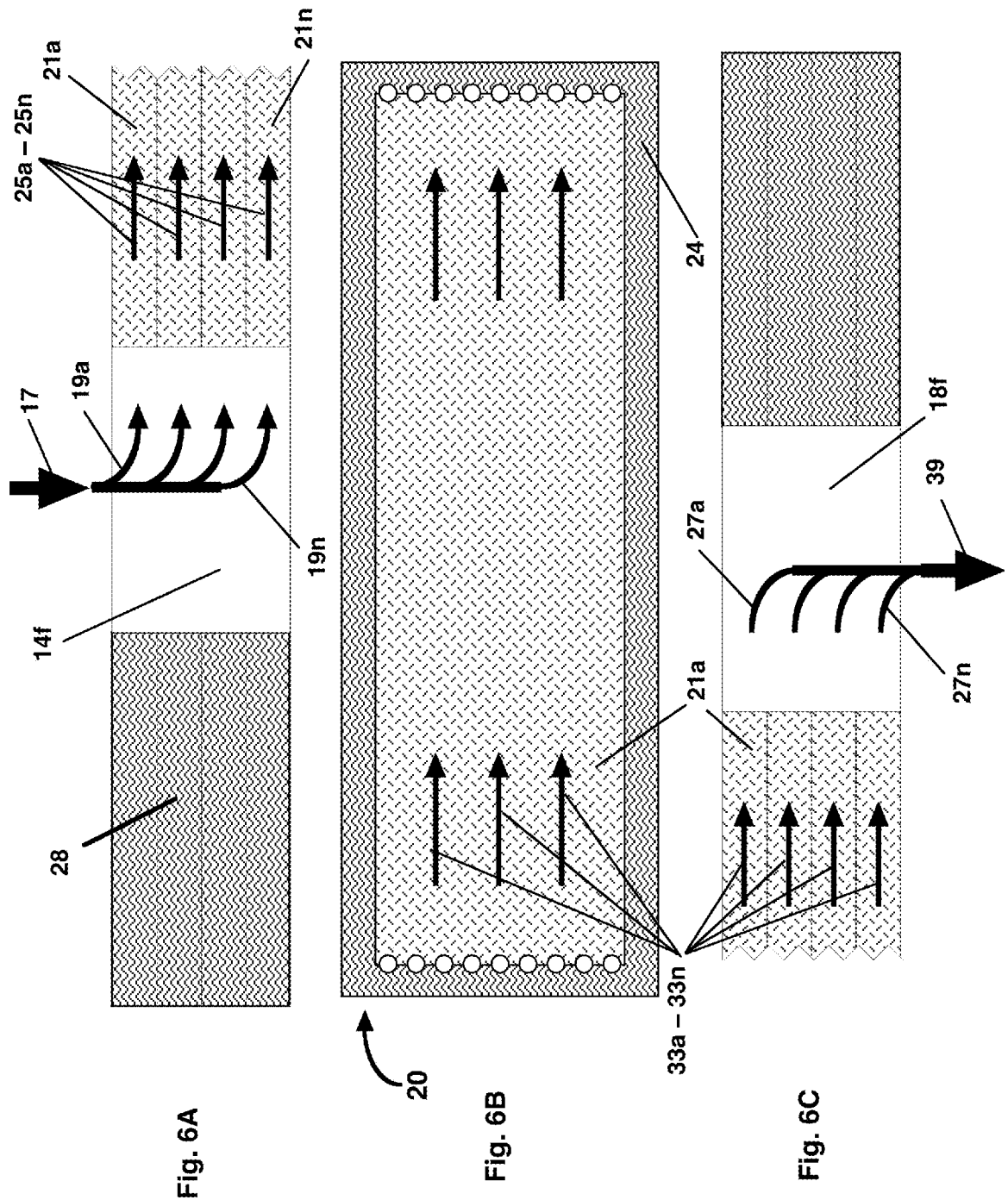
FIGS. 6A-6C are schematic diagrams showing flow profiles in cassettes according to an aspect of the invention.

FIG. 6A shows a magnified section view (through Section 2A on FIG. 1B) of distribution passageway 14f on the feed end of block 20, showing the flow profile of the feed stream within each web 21a-21n. The feed stream (not shown) is distributed along the width of the block by the manifold (not shown) entering each one of several distribution passageways 14 as feed sub-stream 17, which is further distributed and turned forming lateral streams 25a-25n within each web layer. In contrast to filtration devices, lateral streams 25a-25n flow along the plane that defines web 21 (i.e., these flow laterally rather than perpendicularly to the plane of web 21). FIG. 6B shows the flow streamlines 21a-21n in a plan view on web 21, showing the fluid traveling from the feed end towards the eluent end. FIG. 6C shows a magnified section view (through Section 2A on FIG. 1B) of distribution passageway 18f on the eluent end of block 20, further showing how lateral streams 33a-33n within each web layer 21 are collected to form eluent sub-stream 39 within distribution passageway 18f. There are multiple eluent sub-streams 39 that are collected along the width of the cassette by the manifold (not shown) forming the complete eluent stream (not shown) from block 20.

FIGS. 7A and 7B show another embodiment, where the cassette is configured in a circular geometry instead of a rectangular geometry as shown in FIG. 1A. Circularly shaped web 412 has a peripheral edge seal 410 with distribution passageways 404a-404n. In this case the feed distribution passageways 404 are located in the periphery of web 412, whereas the eluent distribution passageway 402 may be a single channel in the center of web 412 (it should be understood that the distribution passageway 402 in the center of the circular web may also comprise two or more distribution passageways 402). Alternatively, the passageway 402 in the center is the feed distributor whereas the passageways 404 near the periphery are the eluent distributors. In this case the fluid flow path is radial, making the length of the flow path approximately equal to the radius of the circularly shaped web 412.

Figure 7:
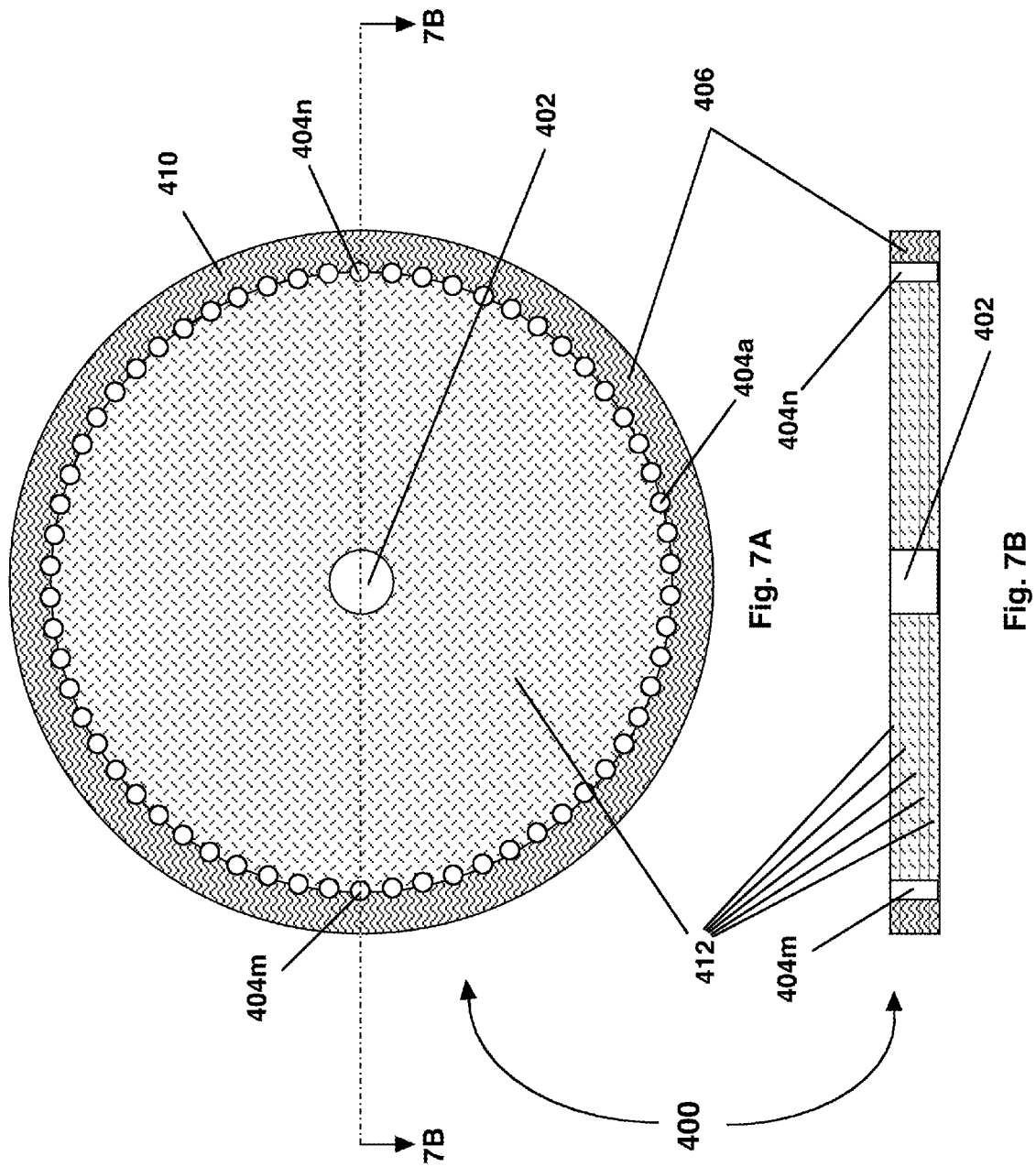
Figure 8:
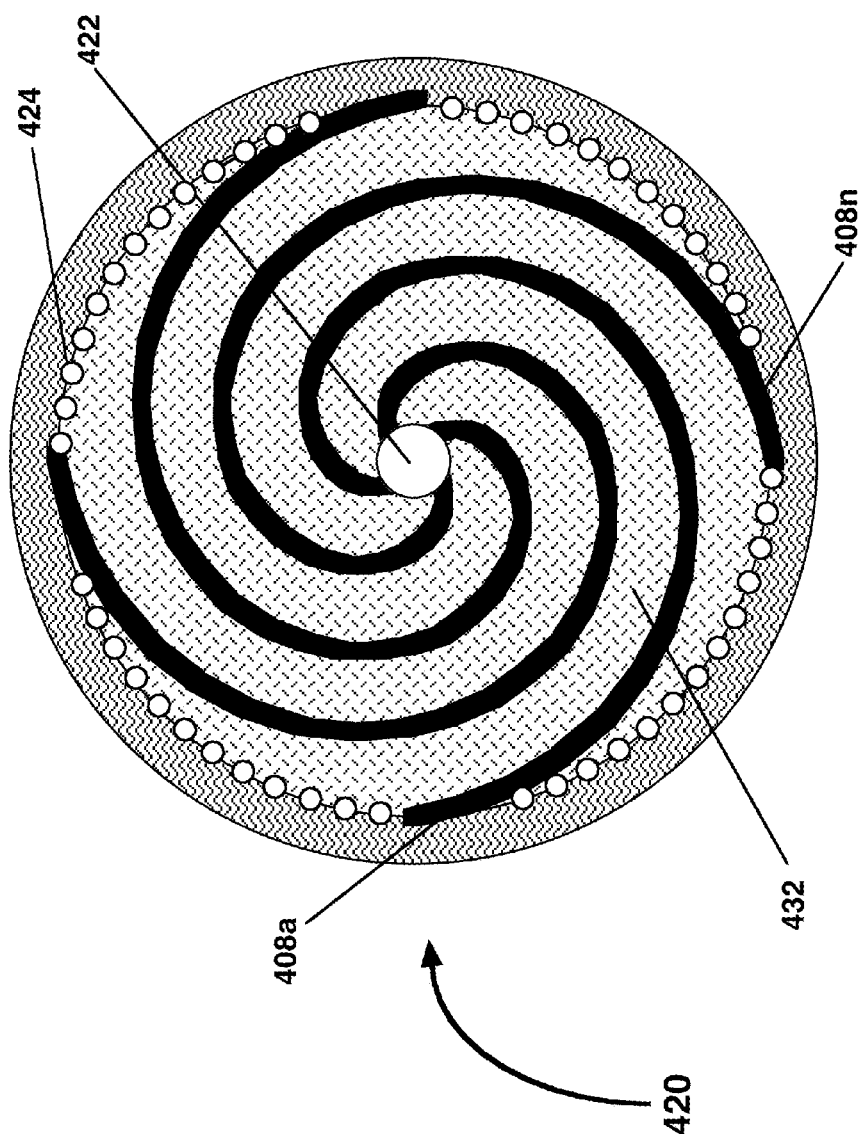

FIG. 8 shows another embodiment of a circularly shaped cassette including ribs 408a-408n that force the fluid to flow in a spiral trajectory forming a longer flow path than that on the embodiment shown in FIG. 7.

Figure 9:
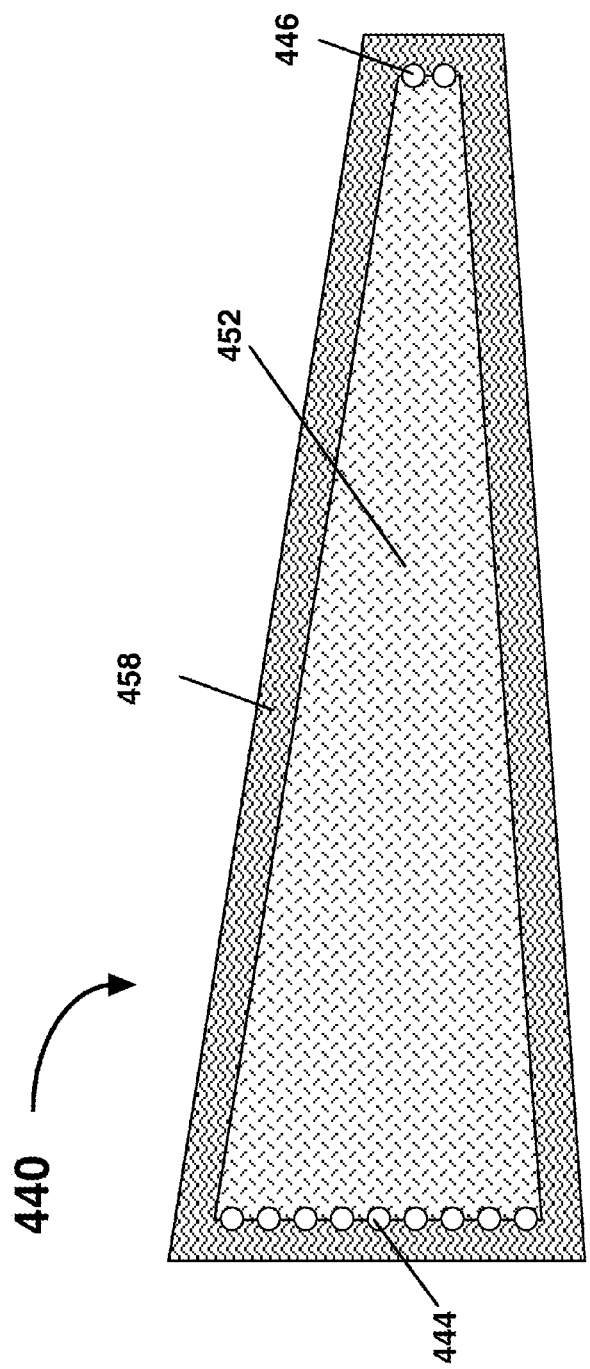

FIG. 9 shows another embodiment of a cassette 440 whose webs 452 are approximately in the shape of a "pie slice" or a trapezoid. Any shape is possible as long as webs 452 are flat, have peripheral edge seal 448 and distribution passageways 444 and 446, the application dictating which shape is most beneficial. Also, in general it should be understood that ribs (not shown) can be utilized in any geometry, circular, rectangular or otherwise, to channel the fluid in trajectories which may be different from the natural trajectory that a fluid would travel within the webs 452.

FIGS. 10A-10C show a cassette 500 according to one embodiment devices disclosed herein made with an adsorptive media in the form of a monolith 522 instead of multiple web layers, the key difference being that monolith 522 is much thicker than a web, such that a single monolith creates a substantial height (only possible with multiple layers when using webs). According to this embodiment monolith 522 comprises peripheral edge seal 506 and distribution passageways 508, FIG. 10B showing a cassette made with a monolith thinner than that shown in FIG. 10C. Just as has been described in FIGS. 1 through 7B, cassettes of the same geometries and possibilities can be made with monoliths 522 as long as these have flat top and bottom surfaces and have sufficient tensile and compressive strength to support the hydraulic forces generated in use. Monoliths create the option of adding a seal to the flat top and bottom surfaces capable of restraining the hydraulic forces generated in use. In this case the top and bottom plates become optional since the cassette is self-supporting; furthermore, the end plates only need to attach to the feed and eluent distributors in cassette 500.

FIG. 11A shows a plan view of another embodiment of a rectangularly-shaped cassette in which the cassette is "double-sided". In this embodiment the cassette includes another set of distribution passageways 516 at the center point of the length dimension of web 512 in addition to the set of distribution passageways 504 and 508 at the two ends of the cassette 500. Referring to FIG. 11A cassette 550 comprises webs 512 with peripheral edge seal 513 having a set of center distribution passageways 516 at the center point of the length dimension of web 512, and two sets of distribution passageways 504 and 508 at the two ends of web 512. In this particular embodiment center passageways 516 distribute the feed stream, while end passageways 504 and 508 collect the eluent stream. Flow profiles for this embodiment are shown in FIG. 11B. In an alternative embodiment of a double-sided cassette (not shown), distribution passageways 504 and 508 distribute the feed streams while center passageways 506 collect the eluent streams.

FIGS. 12A-12E represents in schematic manner an exemplary process to fabricate the cassette shown in FIG. 1A. A plurality of webs 600 are cut to a desired dimension as shown FIG. 12A and stacked as shown in FIG. 12B. A peripheral edge seal 606 is created by one of many methods known to those skilled in the art (e.g., a thermoset resins or thermoplastic resin or other sealants known to those skilled in the art can also be used) as shown in FIG. 12C. Once cured, the stack of webs 600 is perforated (by drilling, die cutting, laser cutting or other methods known to those skilled in the art) to form substantially straight distribution passageways 604 and 608 in the height dimension as shown in FIG. 12D, resulting in finished cassette 620 of FIG. 12E.

There are many variations to this fabrication method. For example, the distribution passageways may be perforated on each individual web 650 before these are stacked; this method allows the formation of distribution passageways that are not identically located in each web 650, which is acceptable as long as the distribution passageways 654 and 658 have some overlap enabling fluid communication when adjacent webs 650 and 660 are stacked, as shown in FIGS. 13A and 13B. Referring to FIG. 13A, web 650 is perforated with oblong distribution passageways 658, which are not centered in the width dimension but are closer to one edge of web 650 than the other edge, whereas web 660 shown in FIG. 1B is perforated with the same oblong distribution passageways 658 which are also not centered (according to offset 655), but displaced towards the opposite edge of web 660. When adjacent webs 650 and web 660 are stacked, the distribution passageways 654 and 658 do not line up perfectly on top of each other, but do overlap to still create a distributor that is in fluid communication. It should be appreciated that perforating the web 650 with distributor passageways 654 before stacking the webs provides a large flexibility in the formation of the distributors which may be of advantage in some applications. Likewise it may be advantageous to add peripheral edge seal 662 to each web individually before these are stacked.

Distributors may add to band spreading, a phenomenon that deteriorates the effectiveness of chromatographic separation, a deterioration that increases as the hold-up volume of distributors becomes larger relatively to the volume in the separation medium. Therefore, distributors should be designed to have the lowest volume. However, this needs to be balanced with the pressure drop generated by a distributor, which becomes larger the smaller the diameter of the distribution passageways. In many cases, it is possible to maintain the distributor volume to be small relative to the rest of the adsorptive medium, and in such cases, it does the exact distribution pattern of the feed and eluent streams within the distributor has little impact on the separation performance of the devices. In such cases, it is of little consequence where the fluid enters and exits the cassette.

Another approach to reduce the deterioration produced by distributors is to design them such that the bands are not distorted, even when the distributor volume is not small. This requires that every streamline within the passageway separation device (the separation media and the distributor, including the flow passages/distributors contained within the end plates) have the same residence time. For devices disclosed herein, wherein the feed stream comes from a point source and the eluent stream goes back to a point source, the location of entry and exit of the feed and eluent streams, respectively, may be important, leading to preferred embodiments for the distributor design. In the case of rectangular devices disclosed herein (e.g. as shown in FIG. 1 through 4), to maintain the residence time at every streamline as uniform as possible in the presence of significant hold-up volume in the distributors the design principle that should be followed is this: there should be mirror image symmetry in the flow pattern of the feed and eluent streams as they enter and exit the cassette along any plane bisecting the cassette in any of its dimensions. Specifically, this means two things: first, the feed and eluent streams should be located in opposing end plates, and secondly, the feed stream should enter the top (or bottom) end plate on the side opposite to that in which the eluent stream exits the opposite end plate.

FIGS. 14A, 14B and 14C show a device 700 comprising a cassette assembly according to one aspect disclosed herein with end plates designed according to the design principle described in the previous paragraph. FIG. 14A shows a sectional side view of cassette assembly 700, with top end plate 706a, a first gasket 705a, cassette 702, a second gasket 705b, and bottom end plate 706b. In this schematic diagram, top end plate 706a is used to introduce the feed stream, whereas bottom end plate 706b is used to recover the eluent stream. Flow passages 716a inside top end plate 706a is used to distribute the feed stream to distributor passageways 704a in cassette 702. Flow passages 716b inside bottom end plate 706b are used to collect the eluent stream from distributor passageways 704b in cassette 702. FIG. 14B is a front view of a cassette assembly 700 taken along section 14B in FIG. 14A. Referring to FIG. 14B, feed stream 707 enters end plate 706a at feed port 717, and then is further distributed along the width of the device utilizing flow passages 716a. Referring now to FIG. 14C, eluent stream 709 exits end plate 706b at eluent port 719, after having been collected along the width of the device utilizing flow passages 716b. FIGS. 14A, 14B and 14C clearly show that feed and eluent flow passages in end plates 706a and 706b are in mirror image symmetry one to the other as described in the previous paragraph, representing a preferred embodiment whenever the volume of the distributor passageways 704a and 704b in the devices disclosed herein lead to decreased separation performance. It should be further noticed that in this embodiment the flow direction of the feed and eluent streams is the same at every point within cassette assembly 702.

Figures 15A, 15B:
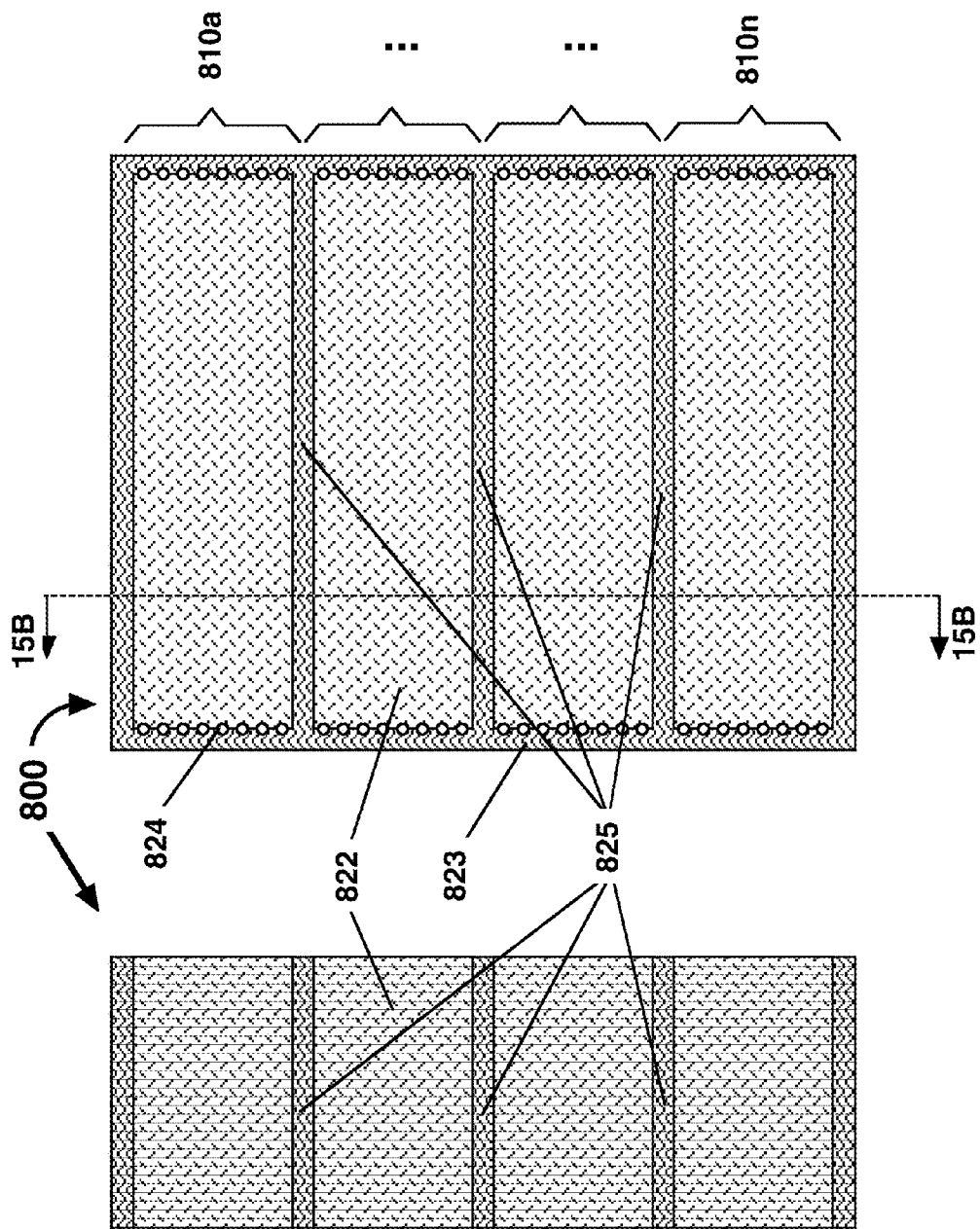
FIGS. 15A, 15B, 16A and 16B are schematic diagrams showing the multiplexed cassettes according to aspects of the invention.

FIGS. 15A and 15B show another embodiment disclosed herein, according to which multiple cassettes 810a-819n are integrated into a single multiplexed cassette 800. Block 822 has peripheral edge seal 823 and further partitioned into multiple cassettes 810a-810n by means of inter-cassette seals 825. Distribution passageways 824 are perforated along the height of block 822 on both ends of block 822 in the manner shown in FIG. 15A. In this embodiment block 822 of multiplexed cassette 800 is built from a stack of multiple layers of web (not shown). Peripheral edge seals 823 and inter-cassette seals 825 are adhered to webs such that these can sustain the internal pressures present in cassettes 810a-810n during use. In another embodiment the media used to form the adsorptive block 822 may be in the form of a monolith (not shown) instead of webs.

Figure 16A:
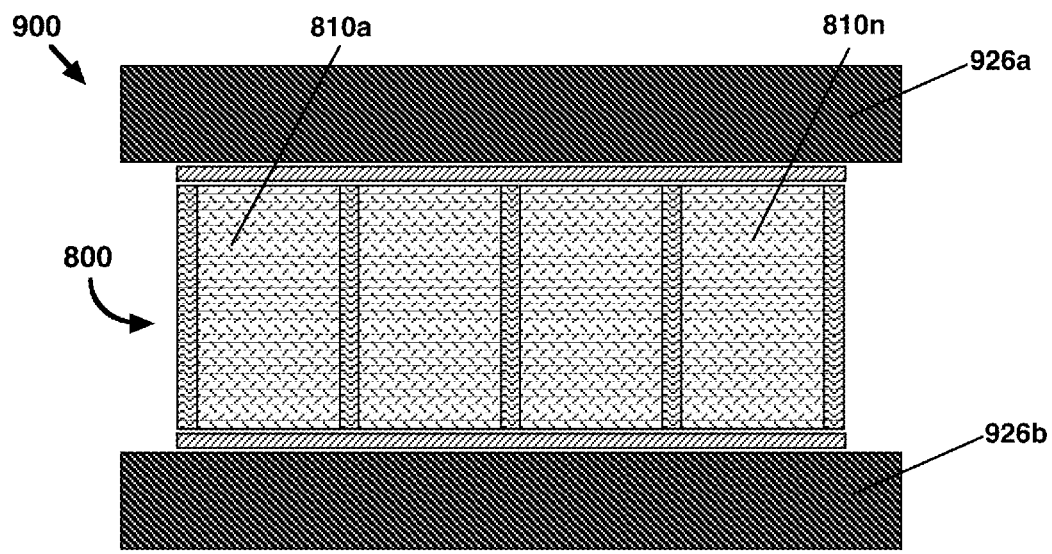
Figure 16B:
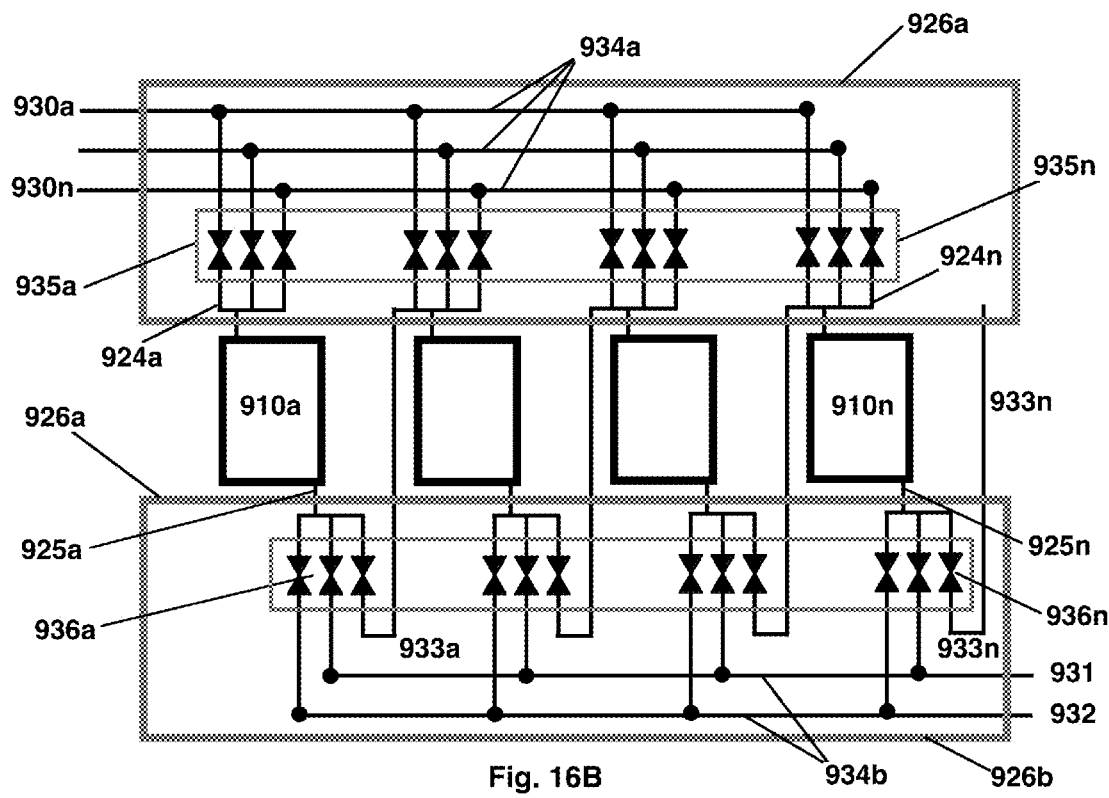

FIG. 16A is an elevation view of a multiplexed cassette 800 in combination with end plates 926a and 926b forming multi-cassette assembly 900. FIG. 16B is a schematic flow diagram of multiplexed cassette assembly 900. End plate 926a includes multiple passageways 934a for introducing multiple feed streams 930a-930n and an array of valves 935a-935n for diverting each feed stream into the manifold 924a of each one of cassettes 810a-810n. End plate 926b includes multiple passageways for collecting multiple eluent streams 934b from each one of cassettes 810a-810n and an array of valves 935b for diverting each eluent stream from the eluent distributors 924b into either a product stream 931, a waste stream 932, or possibly, a feed stream 933a-933n into another one of cassettes 810a-810n. The passageways and valves are included within the end plate, thereby liberating the user from having to make individual connections to each individual cassette 810a-810n. The process design dictates which valves are opened and closed, with a control system (not shown) that opens and close the valves accordingly. In some embodiments the end plates 926a and 926b are reusable. In other embodiments end plates 926a and 926b may be integrated with the cassette to form a completely disposable assembly 900, in which case valves 935a and 935b may be pneumatically actuated, with the pneumatic streams actuated by an array of reusable valves (not shown) connected to the disposable cassette assembly 900 by simple, quick-connect means known to those skilled in the art. This embodiment would be suitable for applications where cross-contamination between batches can't be tolerated, or where the cost of cleaning and validating the cleaning cycle is cost or time prohibitive, or when the safety of operating personnel demands that there be no exposure to the fluid streams.

In other embodiments adsorptive beds designed to receive a liquid flow as described below in conjunction with FIGS. 17A-23B can be used to form planarly cohesive adsorptive blocks or can be used in chromatography columns. In these embodiments the composite adsorptive bed includes a scaffold with open cells (also referred to as void spaces) and adsorptive beads occupying the void space created by the scaffold. The scaffold provides the planar cohesion required by the planar adsorptive devices, and the adsorptive beads provide the desired adsorptive properties. In embodiments utilizing chromatography columns, the scaffold provides structural support to prevent the beads from being crushed, and the adsorptive beads provide the desired adsorptive properties. FIGS. 17A through 22B show examples of planarly cohesive separator sheets suitable for scaffolds for both planar adsorptive devices and chromatography columns, as described below.

Figure 23A:
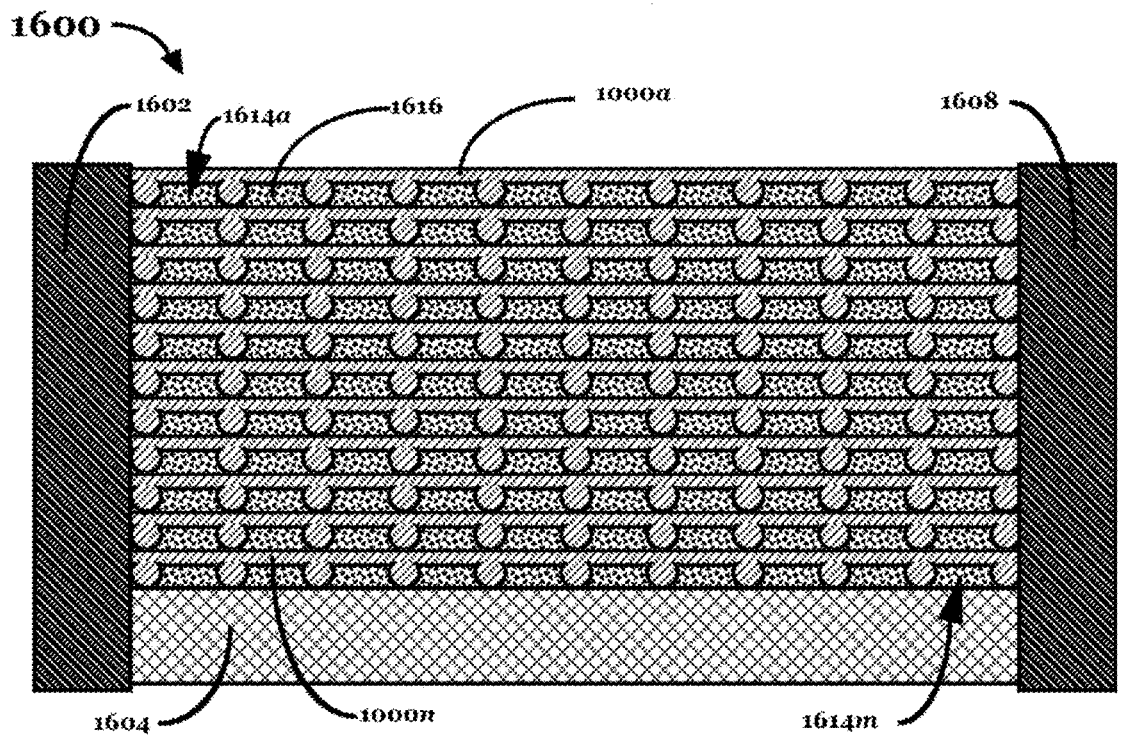
FIG. 23A is a schematic diagram of a scaffold formed by stacking planarly cohesive separator sheet aligned and in intimate contact with adjacent sheets according to aspects of the invention.
Figure 23B:
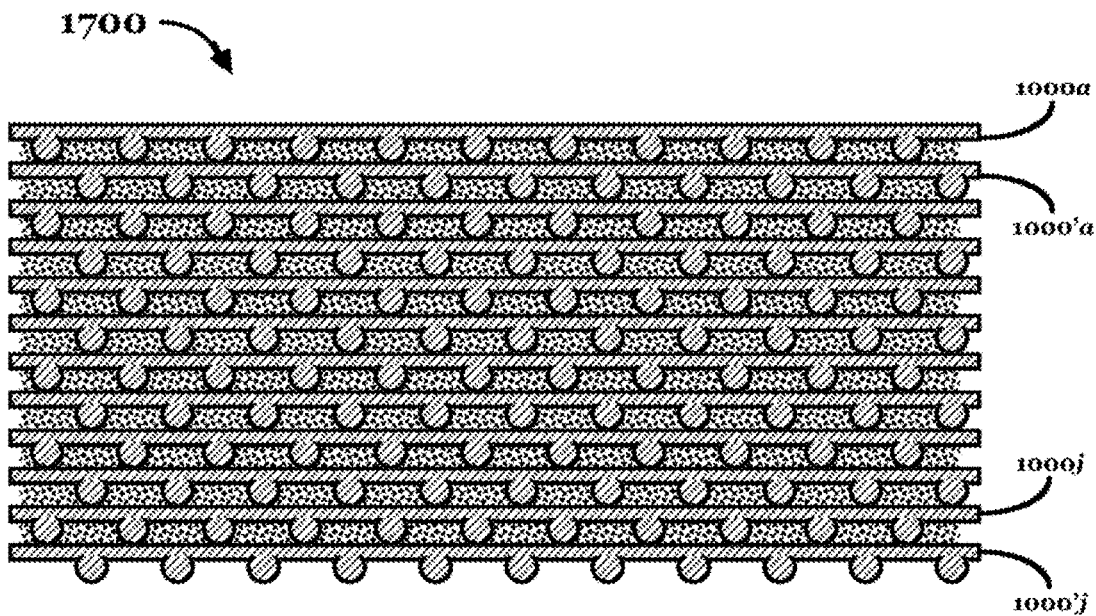
FIG. 23B is a schematic diagram of a scaffold formed by stacking planarly cohesive separator sheet staggered and in intimate contact with adjacent sheets according to aspects of the invention.
Figures 26A, 26B:
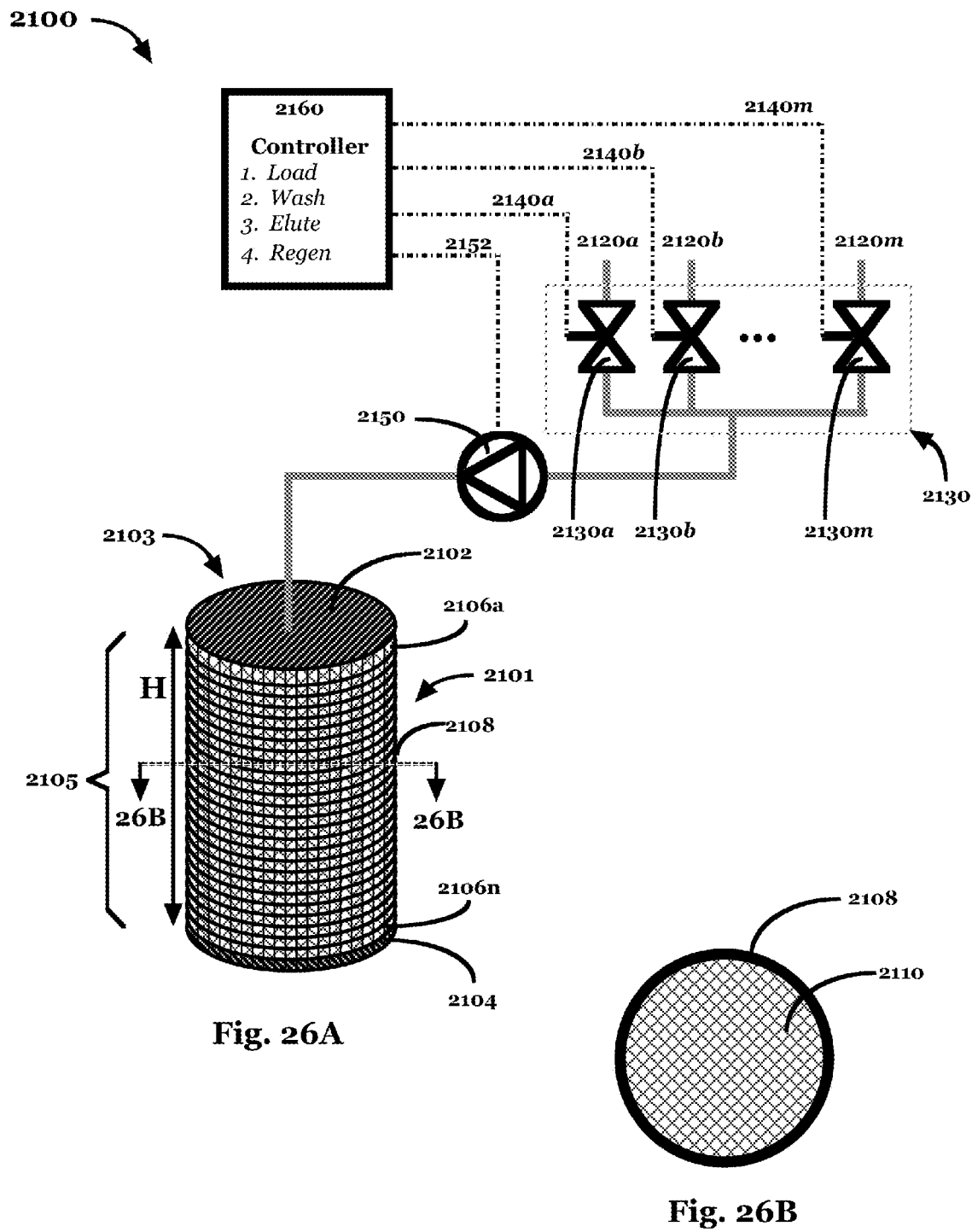
FIG. 26A is a schematic diagram showing a adsorptive bed having a rigid structure scaffold of stacked planarly cohesive separator sheets packed into a chromatography column coupled to a quick cycle controller according to aspects of the invention.
FIG. 26B is a schematic diagram showing a cross section of the chromatography column taken along section 26B-26B of FIG. 26A.

Now referring to FIG. 17A, a planarly cohesive separator sheet 1000 includes a plurality of rigid structural members 1010a-1010n (generally referred to as members 1010) and rigid structural members 1012a-1012m (generally referred to as members 1012) arranged to define the plurality of open cells 1014. The planarly cohesive separator sheet 1000, when stacked together form a stress absorbing substantially rigid structure of a scaffold as shown in FIGS. 23A and 23B. The planarly cohesive separator sheet 1000 can also be stacked in a chromatography column as shown in FIGS. 26A and 26B. In one embodiment, the planarly cohesive separator sheet 1000 comprises a bi-planar plastic net 1000. The bi-planar net 1000 is formed from members 1010 arranged to form a first array of straight members parallel to each other and in a single plane, and members 1012 arranged to form a second array of straight members parallel to each other and in a single plane, wherein the first and second array are perpendicular to each other as shown in FIG. 17A. Here, the rigid structural members are polymeric monofilaments.

FIG. 17B shows a cross-section view of the planarly cohesive separator sheet 1000. In one embodiment the members 1010 and members 1012 are polymeric monofilaments and are fused together at the point of contact, for example, by melting the filaments at the point of contact 1015. The arrangement of members 1010 and members 1012, here fused polymeric monofilaments creates open cells 1014, which enable the packing of adsorptive beads. The planarly cohesive separator sheet 1000 is used to create a stress absorbing substantially rigid structure capable of withstanding compressive and tensile stresses, both of which are present when fluid is pumped creating a liquid flow into a planarly cohesive adsorptive beds or composite adsorptive beds in chromatography columns.

Substantially rigid as used herein, generally means that the deformation of the rigid structural members and the whole scaffold under the stress loads encountered in the application is sufficiently small to be imperceptible in the performance of the adsorptive bed. Functionally this generally means that the adsorptive bed does not move under the applied stresses and, therefore, does not experience voiding, channeling or increased hydraulic resistance due to crushing of the beads. Substantially rigid structural members and their corresponding scaffolds absorb the stresses induced within the composite adsorptive bed by the pressure gradients created by liquid flowing through the bed, thereby preventing these stresses from blowing apart the peripheral seals in stackable planar adsorptive devices, or crushing the beads in conventional chromatography columns. Hereafter "rigid" means "stress absorbing substantially rigid," when referring to either structural members, separator sheets or scaffolds.

Now referring to FIG. 18A, a planarly cohesive separator sheet 1100 similar to the planarly cohesive separator sheet 1000 of FIG. 17A includes a woven screen 1104 with a plurality of rigid structural members 1110a-1110n (generally referred to as members 1010) and a plurality of rigid structural members 1112a-1112m (generally referred to as members 1012) woven together to define the plurality open cells 1114. Here the woven screen 1104 is formed with two arrays of parallel polymeric monofilaments, each array of filaments running in a direction perpendicular to the other and woven together.

FIG. 18B shows a cross-section view of the planarly cohesive separator sheet 1100. In contrast to the planarly cohesive separator sheet 1000, the members 1110 and 1112 are woven together and are not fused together. In other embodiments selective fusing of the members 1110 and members 1112 can be used to render the separator sheet 1100 more rigid.

Now referring to FIG. 19A, a planarly cohesive separator sheet 1200, here a molded plate 1200, includes a bottom planar surface 1220, top planar surface (not shown), edge seals 1206 (also referred to as peripheral seals) and spacers 1210a-1210m (generally referred to as spacers 1210). Molded plate 1200 also includes feed distribution passages 1202a-1202n and eluent distribution passages 1204a-1204m to introduce and collect liquid fed to the composite planarly cohesive adsorptive bed and eluent distribution passages 1204a-1204f to collect the liquid after having been exposed to the composite adsorptive bed.

FIGS. 19B and 19C are cross-sectional views of molded plate 1200 showing the beads 1214 packed into the open cells formed by the rigid structure which includes the flat bottom 1220, edge seals 1206 and spacers 1210. Spacers 1210 maintain the spacing between molded plate 1200 and an adjacent molded plate (not shown) when stacked together forming a rigid structure. The open cells of the molded planarly cohesive separator sheet 1200 enables liquid introduced through feed passages 1202 to flow through the composite adsorptive bed and collected by the eluent passages 1204.

Now referring to FIG. 20A a planarly cohesive separator sheet 1300, here an extruded sheet 1300, includes a flat bottom 1312 and spacers 1310a-1310m (generally referred to as spacers 1310). FIG. 20B is a cross-sectional view of extruded sheet 1300 showing the beads 1314 packed into the open cells formed by the rigid structure of the flat bottom 1312 of the of extruded sheet 1300 and spacers 1310. Spacers 1310 maintain the spacing between extruded sheet 1300 and an adjacent extruded sheet (not shown) when stacked together forming a rigid structure. Adsorptive beads 1314 fill the open cells of the extruded sheet 1300.

Now referring to FIG. 21A a planarly cohesive separator sheet 1400, here, a perforated plate 1400, includes a flat bottom 1420, and spacers 1410a-1410m (generally referred to as spacers 1410). Spacers 1410a-1410m are created by perforating a thin plate, wherein the material removed at the perforations remains attached to the flat bottom 1420 of the perforated plate but bent relatively to the plane of the perforated plate. FIG. 21B is a cross-sectional side view of perforated plate 1400 showing adsorptive beads 1414 packed into open cells formed by the rigid structure of the flat bottom 1420 of the perforated plate 1400 and spacers 1410. Spacers 1410 maintain the spacing between perforated plate 1400 and an adjacent perforated plate (not shown) when stacked together forming a rigid structure. The open cells of the perforated plate 1400 enables liquid flow through the perforated plate 1400. FIG. 21C is a cross-sectional side view of perforated plate 1400 in a direction perpendicular to the side view shown on FIG. 21B, whereby the perforations forming the spacers 1410 are being viewed along their flat dimension. The spacers 1410 created by the perforations may be all be aligned or may be staggered to improve the flow uniformity as shown in this example.

Now referring to FIG. 22A a planarly cohesive separator sheet 1500, here, a porous non-woven web 1500 include randomly packed fibers 1510a-1510n, which are bonded into a rigid structure. The rigid structure of non-woven web 1500 includes a plurality of open cells filled with adsorptive beads 1514 forming a composite planarly cohesive adsorptive bed. FIG. 22B is a magnified cross-sectional view of non-woven web 1500 showing the beads 1514 packed in the open cells created by the rigid structure, which restricts movement of the beads. The non-woven web 1500 has a length L and a thickness H. If the thickness H of non-woven web 1500 is very large, e.g., more than 1 cm and even more than 5 cm, then non-woven web 1500 becomes a porous monolith that provides an adsorptive bed without the need to stack a plurality of separator sheets 1500.

In other embodiments, the planarly cohesive separator sheet is formed by randomly packed packing pieces bonded into a planarly cohesive sheet (not shown). Suitable packing pieces can have any shape and size as long as they form a rigid scaffold having void space in the form of open cells. Examples of suitable packing pieces include, but are not limited to, those used in packed distillation and extraction columns (e.g., Rashig rings; Splined Rings; Pall Rings; Berl Saddles; glass shot; Helices; Nutter Rings; Super Plastic Sphere) and any others known to those skilled in the art of distillation and extraction. In some embodiments the same packing pieces used in distillation and extraction columns may be suitable packing pieces for scaffolds disclosed herein; in other embodiments requiring a smaller packing piece, similarly shaped packing pieces but of a smaller dimension are used.

In these embodiments the open cells of the void space have to be sufficiently large to enable the beads to flow into these void spaces and pack them tightly. The size of the open cells can be characterized by the diameter of the largest sphere that can be inscribed inside the open cell. Since the plurality of open cells created by the void space are not identical, the population of open cells can be characterized by their average diameter, hereafter referred to as a characteristic diameter. The open cells of the composite adsorptive beds disclosed herein need to have a characteristic diameter that is at least about 10 times larger than the average diameter of the adsorptive beads in order to enable uniform and effective packing of the open cells of the void space.

FIGS. 23A and 23B are schematic diagrams of composite beds comprising a rigid scaffold formed by stacking separator sheets of the type shown in FIG. 17 and adsorptive beads packed into the open cells created by the rigid structure of the scaffold. Now referring to FIG. 23A, an adsorptive bed 1600 includes a housing 1602 having a first surface 1604 and a scaffold 1606 disposed within the housing in contact with the first surface 1604. The scaffold 1606 includes a stress absorbing substantially rigid structure 1608 and a plurality open cells 1614a-1614n (collectively referred to as open cell 1614) disposed within the rigid structure 1608. The adsorptive bed 1600 further includes a plurality of adsorptive beads 1616 filling the plurality of open cells 1614 forming a packed bed of the plurality of adsorptive beads.

Here, the stress absorbing substantially rigid structure 1608 includes a plurality of stacked planarly cohesive separator sheets 1000a-1000n (collectively referred to as separator sheet 1000), each of the plurality of stacked planarly cohesive separator sheets 1000 being in intimate contact with adjacent ones of the plurality of stacked planarly cohesive separator sheets 1000, and each of the plurality of stacked planarly cohesive separator sheets 1000 include a plurality of rigid structural members arranged to define the plurality open cells 1614.

In one embodiment, the separator sheets 1000 are stacked on top of each other such that the members that form the rigid structure of scaffold 1600 are lined up. Scaffold 1600 has void space in the form of open cells that are filled by adsorptive beads, which are packed into a bed. FIG. 23B is a schematic of another embodiment of scaffolds disclosed herein. Scaffold 1700 is formed by stacking separator sheets of the type shown in FIG. 17. Separator sheets 1000 are stacked on top of each other such that the filaments that form the rigid structure of scaffold 1600 are staggered. Scaffold 1700 has void space in the form of open cells that are filled by adsorptive beads, which are packed into a bed. It should be understood that the separator sheets can be stacked such that the open cells are substantially aligned as in FIG. 23A, or that the open cells are staggered in a repeating sequence as shown in FIG. 23B, or in any various staggered orientations. An important aspect of the stacking is that the scaffold created is substantially rigid and the void spaces of the rigid structure of the scaffold creates a plurality of open cells.

In operation the adsorptive bed 1600 receives a liquid flow and the scaffold 1606 restricts movement of the plurality of adsorptive beads 1614, absorbs compressive stress induced by a hydraulic pressure gradient along a direction of the liquid flow and transfers a portion of the induced compressive stress to the first surface 1604 of the housing 1602.

The planarly cohesive scaffolds and separator sheets described in FIGS. 17A-23B can be used to create composite adsorptive beds suitable for stackable planar adsorptive devices (requiring planarly cohesive adsorptive media), or alternatively, can be used to create composite adsorptive beds suitable for chromatography columns. When used in chromatography columns the composite adsorptive beds disclosed herein enable the use soft beads packed into conventional chromatography columns and operated at pressures substantially higher than in conventional operation. Operating at these high pressures, for example, greater than 100 psi is not possible without the structural support provided by the rigid scaffold. In these embodiments the rigid scaffold of the composite adsorptive bed absorbs the compressive stress created by the liquid flow, whereas the relatively soft adsorptive beads packed into the void space of the rigid structure provide the adsorptive media for the separation. Without the rigid scaffold a large class of soft beads (e.g., agarose and sepharaose beads) cannot be used at high pressures, limiting the length of the column and/or the velocity of the mobile phase used in the chromatographic separation and/or the size of the adsorptive bead that can be used. In one embodiment, the adsorptive bed supports a liquid flow velocity greater than 150 cm/hour.

In planar stackable devices the adsorptive media needs to be planarly cohesive to withstand the hydrostatic pressures within the device as well as the pressure gradients created by the liquid flow. All of the stresses created by liquid flow want to blow apart the device, requiring adsorptive media that is planarly cohesive to withstand the tensile stresses. In contrast, conventional chromatography columns have a rigid housing capable of withstanding the pressure, however, the pressure gradients induced by liquid flow create a compressive stress that must be withstood by the adsorptive bed.

Figure 24A:
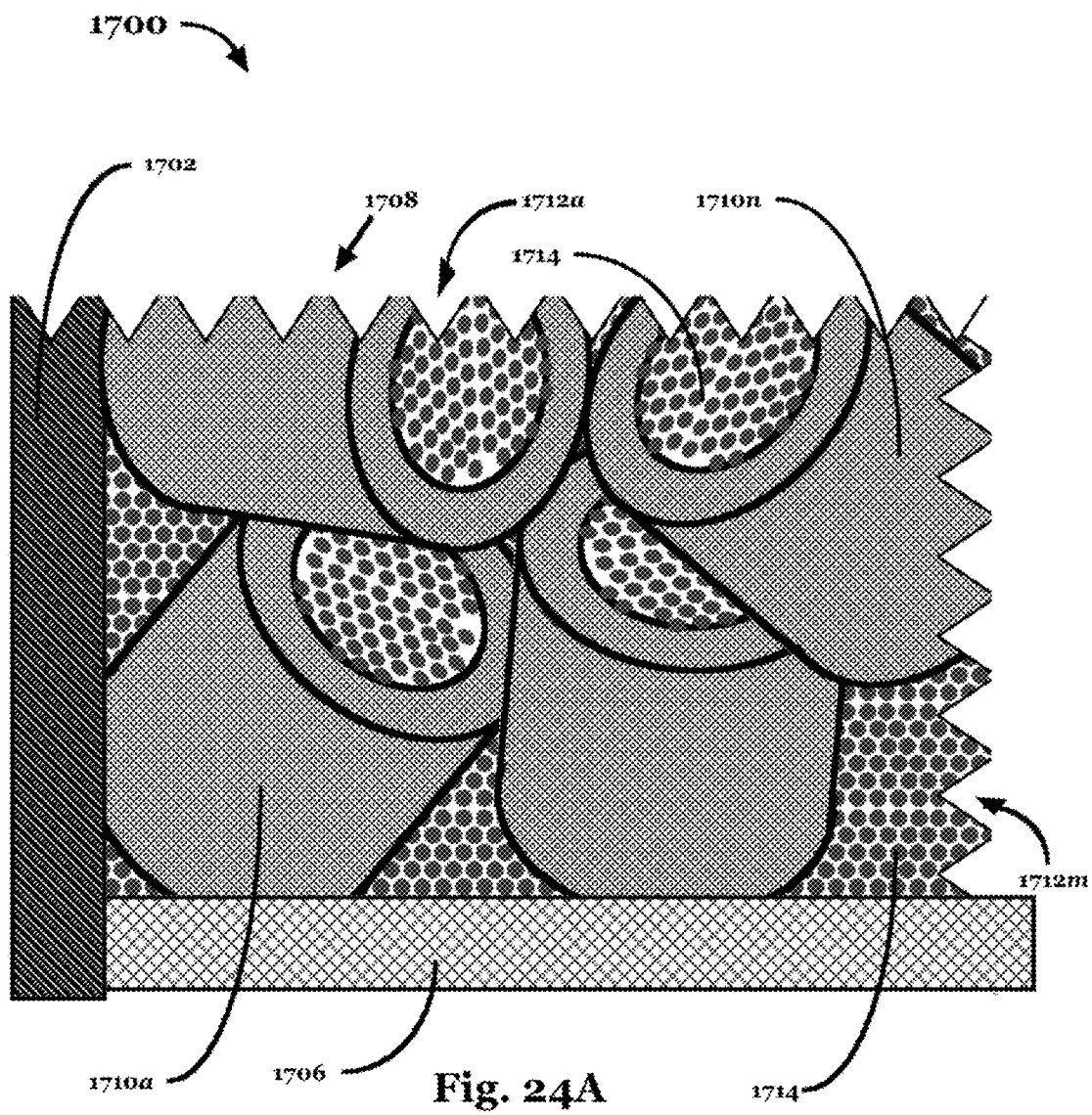
FIG. 24A is a schematic diagram showing a adsorptive bed having a rigid structure comprising a plurality of randomly packed Raschig rings packed into a chromatography column according to aspects of the invention.

FIG. 24A shows a portion of a composite bed 1700 which includes a scaffold 1702 having a rigid structure including a plurality of randomly packed packing pieces 1710a-1710n (collectively referred to as packing pieces 1710). Each one of the plurality of randomly packed packing pieces 1710 is made from a rigid structural material and the plurality of randomly packed packing pieces 1710 are arranged to define the plurality of open cells 1712a-1712m (collectively referred to as open cell 1712) formed by the packing pieces 1710. Here the packing pieces 1710 are Raschig Rings. The packing pieces 1710 include, but are not limited to, a Lessig Ring, a Splined Ring, a Pall Ring, a Berl Saddle, a glass shot, a helix, a Nutter Ring and a Super Plastic Sphere. It is understood that various type of packing pieces 1710 can be intermixed. In one embodiment the plurality of randomly packed packing pieces 1710 are randomly packed one on top of each other in a chromatography column, and beads 1714 packed into the open cell 1712 void space formed by the rigid structure of the scaffold. The packing pieces within a chromatography column form a rigid structure supported by the column bottom 1706 and the column sidewalls 1702. The rigid scaffold restricts the movement of the beads and absorbs the compressive stress created by the liquid flow preventing the beads from getting crushed.

Figure 24B:
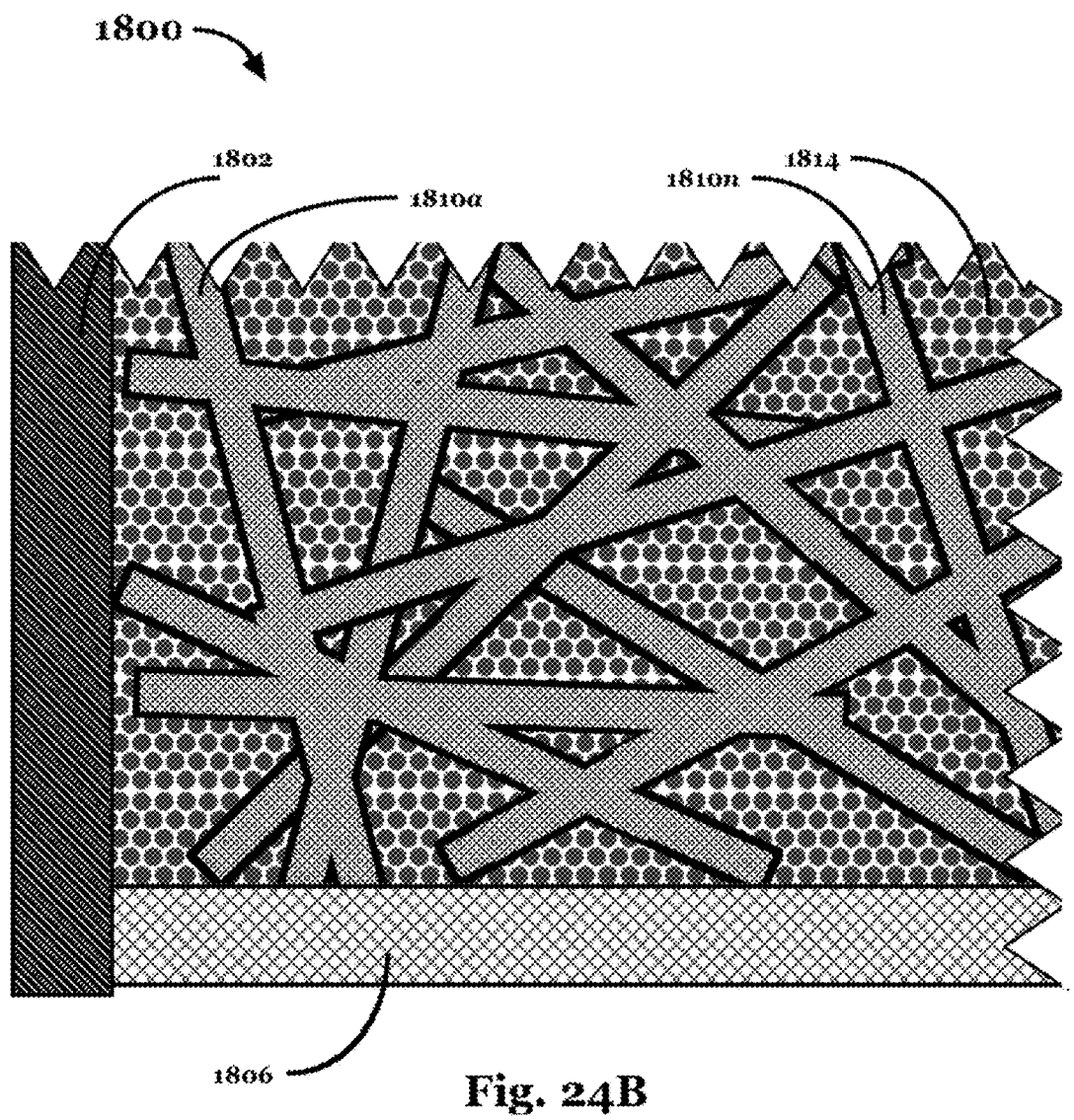
FIG. 24B is a schematic diagram showing a adsorptive bed having a rigid structure comprising a plurality of randomly packed filaments packed into a chromatography column according to aspects of the invention.

FIG. 24B shows a composite bed 1800 comprising a scaffold formed by packing pieces 1810a-1810n (generally referred to as packing pieces 1810), here, filaments which are randomly packed one on top of each other in a chromatography column, and beads 1814 packed into the void space formed by the rigid structure of the scaffold. The packing pieces within a chromatography column form a rigid structure supported by the column bottom 1806 and the column sidewalls 1802. The rigid scaffold restricts the movement of the beads and absorbs the compressive stress created by the liquid flow preventing the beads from getting crushed. In some embodiments packing pieces 1710 and 1810 of composite adsorptive beds 1700 or 1800 can be fused, bonded or sintered together prior to packing the open cells with adsorptive beads (not shown).

Beads may be introduced into the void space by dry packing or slurry packing methods known to those skilled in the art. In some embodiments the beads are introduced into the scaffold gradually as the separator sheets are stacked. In other embodiments the beads are introduced after the whole scaffold is fabricated into a planarly cohesive device or arranged inside the chromatography column. In still other embodiments it may be possible to introduce the adsorptive beads into individual separator sheets.

Figures 25A, 25B:
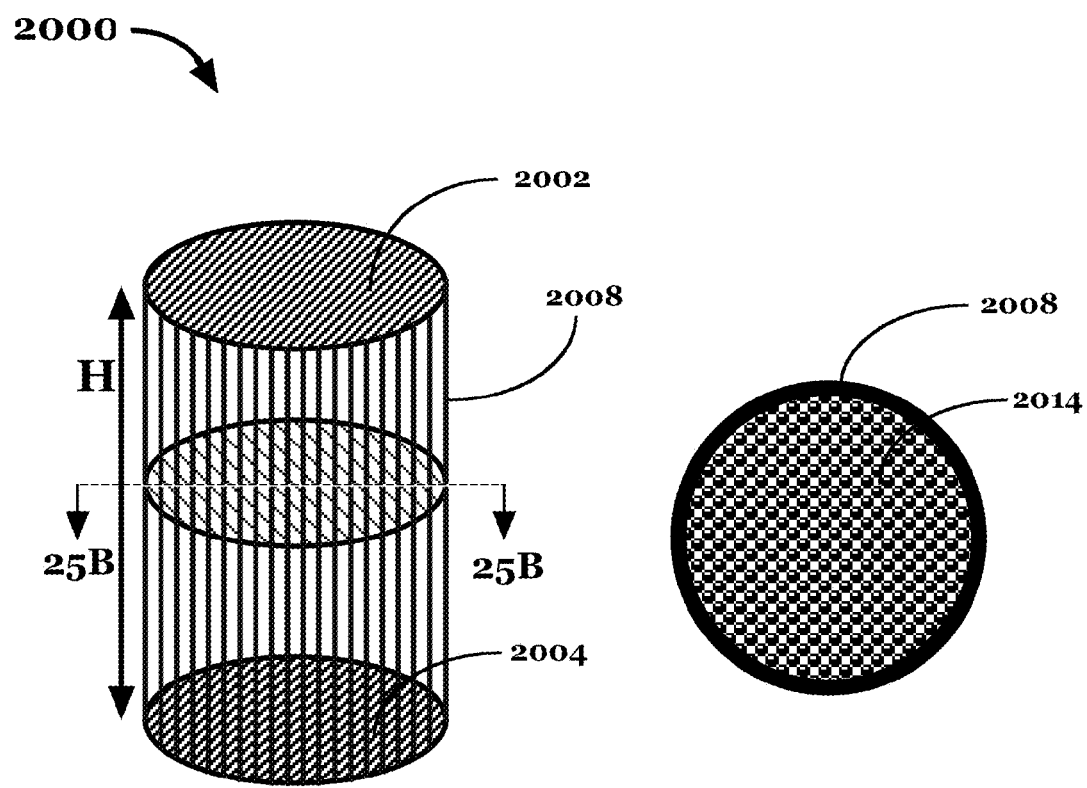
FIGS. 25A-25B are schematic diagrams showing a conventional chromatography column.

FIG. 25A is perspective view of a prior art chromatography column in wire-frame format. Chromatography column 2000 has sidewalls 2008, bottom planar surface 2004 and top surface 2002. Chromatography column 2000 is packed with adsorptive beads (not shown) to form an adsorptive bed of height H. FIG. 25B is a cross-sectional view of column 2000 showing adsorptive beads 2014 supported by sidewalls 2008. In operation column 2000 is fed a liquid to a distributor (not shown) at the top surface 2002. Due to the hydraulic resistance of the adsorptive bed formed by the packing of adsorptive beads 2014, the fluid must be a pumped under pressure, which creates a hydrostatic pressure within the column 2000 as well as a pressure gradient. The forces developed by the hydrostatic pressure are restrained by the sidewalls 2008 and top and bottom surfaces 2002 and 2004, respectively. The pressure gradient created by each layer of beads in the packed bed builds a compressive stress on the packed bed that increases along the flow direction of the liquid. As a result, the beads at the bottom of the packed bed, adjacent to the bottom surface 2004, are being compressed by the hydraulic pressure gradient from the top to the bottom surfaces, hereafter referred to as the pressure drop. Soft agarose and sepharose beads commonly used in the purification of biomolecules start to deform when subjected to compressive pressures of about 25~50 psi. For this reason chromatography columns packed with these types of soft beads can't be operated at flow rates that generate pressure drops within the column that exceed 50 psi, and preferably 30 psi. The compressive stress limitation of soft beads significantly limits the conditions at which such chromatography columns can be operated. More specifically, such columns must be relatively short (e.g., typically less than 50 cm), must be operated at relatively low flow velocities (e.g., typically less than 150 cm/hr) and must utilize relatively large beads (e.g., typically not less than 90~100 μm in diameter). The net result is that chromatography columns are difficult to scale up, and the processes have a low productivity leading to large columns and/or long processing times.

Now referring to FIG. 26A, a chromatography system 2100 includes an adsorptive bed 2105 including scaffold 2101, here packed into a chromatography column 2103 acting as a housing. The chromatography system 2100 further includes a rapid cycling controller 2160, at least one pump 2150 and at least one valve 2130a controlling a liquid feed stream. The rapid cycling controller 2160 is coupled via control line 2152 to the pump 2150 and control line 2140a to valve 2130a controlling a liquid feed stream. It is understood that multiple pumps and valves 2130a-2130n with corresponding control line 2140a-2140n can be used to control the system. The chromatography column 2103 includes sidewalls 2108, bottom surface 2104 and top surface 2102. Column 2103 is packed with a composite adsorptive bed 2105 comprising a rigid scaffold 2101 having void space in the form of open cells, and adsorptive beads (not shown) packed into the open cells as shown in the embodiments described in FIGS. 17 to 24. The scaffold 2101 disposed within the chromatography column housing 2103 is in contact with the bottom surface 2104 (also referred to as the first surface). The scaffold 2101 acts as a rigid structure absorbing the compressive stress induced on the adsorptive bed along a direction of the liquid flow (indicated along the double arrow labeled "H"). The scaffold 2101 restricts movement of the plurality of adsorptive beads, absorbs compressive stress induced by hydraulic pressure gradient along the direction of the liquid flow and transfers a portion of the stress to the first surface of the housing, here, the bottom surface 2104 of the chromatography column housing 2103.

In one embodiment the rigid scaffold 2101 comprises a stack of separator sheets 2106a-2106n (collectively referred to as separator sheets 2106) that have been cut to the same shape (i.e., diameter) as the interior diameter of the chromatography column. The stack of separator sheets 2106 fills the interior of the chromatography column creating a rigid scaffold of height H, with void space in the form of open cells packed with adsorptive beads (not shown). FIG. 26B is a cross-section view of column 2103 showing sidewalls 2108 and composite adsorptive bed 2110 comprising a rigid scaffold comprising with open cells formed by separator sheets 2106, and adsorptive beads (not shown) packed into the open cells. In other embodiments, the scaffold 2101 is similar to the scaffolds shown in FIGS. 24A and 24B.

In contrast to the chromatography columns of the prior art, the rigid scaffold restricts the movement of the adsorptive beads and absorbs the compressive stress generated by the pressure gradients generated by the adsorptive bed, enabling the utilization of soft beads in columns having pressure drops exceeding 100 psi. Such pressures are generated when beads smaller than 100 μm are packed into columns that are longer than 50 cm and/or operated at mobile phase velocities exceeding 150 cm/hr. In some embodiments pressure drops greater than 300 psi are generated, which may be necessary when utilizing soft beads smaller than 50 μm in diameter. In still other embodiments pressure drops greater than 300 psi are generated, which may be necessary when utilizing soft beads smaller than 25 μm in diameter.

In operation, chromatography system 2100 feeds the chromatography column 2103 using the pump 2150. In one embodiment the pump 150 is capable of generating pressures exceeding 100 psi. The rapid cycling controller 2160 controls the pump 2150 and valves 2130a-2130m (collectively referred to as valve array 2130) by means of control lines 2140a-2140m (collectively referred to as control lines 2140). Valve array 2130 selects one of several feed streams 2120a-2120m (collectively referred to as feed streams 2120) as necessary to effect a multi-step chromatography process. Multi-step chromatography processes typically utilize at least four feed streams 2120, which are fed sequentially to effect at least four steps: load; wash; elute; and regenerate. These streams are fed at varying mobile phase velocities and for varying times following conditions selected by the rapid cycling controller 2160. In one embodiment, a purification process includes adsorbing target solute in the adsorptive bed, washing non-adsorbed solutes, releasing purified target solute, and conditioning the adsorptive bed for a next purification cycle.

The sequence of steps in such multi-step chromatographic processes is required to yield the desired purified solute; therefore, the multi-step sequence has to be exercised at least once in order to obtain a purified solute. It is possible to carry out the multi-step sequence more than once for a given manufacturing batch in order to process a larger amount of feed stream utilizing a chromatography column that is not capable of adsorbing the full batch in one step. In this manner, a smaller chromatography column can be used to process amounts that would require a larger column. Such multi-cycle chromatography processes are increasingly common, typically cycled two to five times. It would be particularly advantageous to cycle a chromatography column a dozen times with a single manufacturing batch, and even more advantages to cycle the column more than 100 times, since the larger the number of cycles the smaller the column and the lower the cost. Although such rapid cycling processes are clearly advantageous to reduce the cost of a chromatographic column, and in particular, the cost of adsorptive media, rapid cycling is only possible with smaller diameter beads operated at high mobile phase velocities. Adsorptive beds having scaffolds with rigid structures as described above restrict the movement of the adsorptive beads and support them to enable rapid cycling chromatography processes utilizing soft beads.

Although the term "bead" generally refers to a particle in the form of a small sphere, it should be understood that the term adsorptive beads as used in this invention refers to adsorptive particles that may or may not be spherical. The materials comprising the scaffolds include, but are not limited to, plastic, metal or ceramic materials.

Referring again to FIG. 26A, in some embodiments pump 2150 can pump the liquids at pressures exceeding 300 psi, and the adsorptive bed can include adsorptive beads having diameters of approximately 50 μm. In still other embodiments pump 2150 can pump the liquids at pressures exceeding 500 psi the adsorptive bed can include adsorptive beads having diameters of approximately 25 μm. In some embodiments separator sheets 2106 may be stacked from the bottom surface 2104 to the top surface 2102 to create the rigid scaffold. To make sure the scaffold is sufficiently rigid the stack of separator sheets 2106 may be pre-compressed to a compressive stress that exceeds the anticipated pressure drop at which the column 2103 will be run before the top surface 2102 is attached to the column sidewalls 2108. The adsorptive beads may be packed into the open cell created by the rigid scaffold by pumping a slurry of beads through the column 2103 utilizing methods know to those skilled in the art. In such slurry packing process the beads gradually fill the void space in layers from bottom surface 2104 to top surface 2102 as the slurry is pumped through the column until the composite adsorptive bed becomes fully packed.

It is understood that although the embodiments described herein relate specifically to bio-molecular applications, the principles, practice and designs described herein are also useful in other applications, including the manufacture of vaccines and biopharmaceuticals. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. An adsorptive bed to receive a liquid flow comprising:
   a housing having a first surface;
   a scaffold disposed within the housing in contact with the first surface comprising:
      a stress absorbing substantially rigid structure; and
      a plurality of open cells disposed within the rigid structure;
   a plurality of adsorptive beads filling the plurality of open cells forming a packed bed of the plurality of adsorptive beads;
   wherein the scaffold restricts movement of the plurality of adsorptive beads, absorbs compressive stress induced by a hydraulic pressure gradient along a direction of the liquid flow and transfers a portion of the induced compressive stress to the first surface of the housing; and
   wherein the rigid structure comprises a plurality of stacked planarly cohesive separator sheets, each of the plurality of stacked planarly cohesive separator sheets being in intimate contact with adjacent ones of the plurality of stacked planarly cohesive separator sheets, each of the plurality of the stacked planarly cohesive separator sheets comprising a plurality of rigid structural members arranged to define the plurality of open cells.

2. The adsorptive bed of claim 1, wherein each planarly cohesive separator sheet comprises one of:
   a bi-planar plastic netting;
   a woven screen;
   a molded plate;

an extruded sheet;

a perforated plate; and a sheet of randomly packed packing pieces bonded into a planarly cohesive sheet.

3. The adsorptive bed of claim 1, wherein the first surface is a sidewall of the housing and the housing further comprises:

a top planar surface;

a bottom planar surface;

a peripheral seal bonded to the plurality of stacked planarly cohesive separator sheets at the sidewall; and wherein the liquid flow is along a plane of the plurality of stacked planarly cohesive separator sheets.

4. The adsorptive bed of claim 1, wherein the housing comprises a chromatography column;

wherein the first surface is a bottom of the chromatography column; and wherein the liquid flow is perpendicular to the plurality of planarly cohesive separator sheets and to the bottom of the chromatography column.

5. The adsorptive bed of claim 1, wherein the scaffold has a compressive strength greater than 100 psi.

6. The adsorptive bed of claim 5, wherein the adsorptive bed supports a liquid flow velocity greater than 150 cm/hour.

7. The adsorptive bed of claim 1, wherein each of the plurality of open cells has a characteristic diameter at least ten times larger than the characteristic diameter of the plurality of adsorptive beads.

8. The adsorptive bed of claim 1, wherein each of the plurality of adsorptive beads has a diameter of less than 100 microns.

9. An adsorptive bed to receive a liquid flow comprising:

a housing having a first surface;

a scaffold disposed within the housing in contact with the first surface comprising:

a stress absorbing substantially rigid structure; and a plurality of open cells disposed within the rigid structure;

a plurality of adsorptive beads filling the plurality of the open cells forming a packed bed of the plurality of adsorptive beads;

wherein the scaffold restricts movement of the plurality of the adsorptive beads, adsorbs compressive stress induced by a hydraulic pressure gradient along a direction of the liquid flow and transfers a portion of the induced compressive stress to the first surface of the housing, and wherein the rigid structure comprises a plurality of randomly packed packing pieces, each one of the plurality of randomly packed packing pieces comprising a rigid structural material and the plurality of the randomly packed packing pieces arranged to define the plurality of the open cells.

10. The adsorptive bed of claim 9, wherein each of the plurality of random packing pieces comprises one of:

Raschig rings;

Lessig rings;

splined rings;

Pall rings;

Berl saddles;

glass shot;

helices;

Nutter rings; and

Super Plastic spheres.

11. The adsorptive bed of claim 9, wherein the adsorptive bed is packed into a chromatography column.

12. An adsorptive bed to receive a liquid flow comprising:

a housing comprising a peripheral seal;

a scaffold disposed within the housing in contact with the peripheral seal comprising:

a stress absorbing substantially rigid planarly cohesive structure; and a plurality of open cells disposed within the rigid structure;

a plurality of adsorptive beads filling the plurality of open cells forming a packed bed of the plurality of adsorptive beads;

wherein the peripheral seal is bonded to the scaffold; and wherein the scaffold restricts movement of the plurality of adsorptive beads, absorbs compressive stress induced by a hydraulic pressure gradient along a direction of the liquid flow and transfers a portion of the induced compressive stress to the peripheral seal of the housing.

13. The adsorptive bed of claim 12, wherein the scaffold has a compressive strength greater than 100 psi.

14. The adsorptive bed of claim 13, wherein the adsorptive bed supports a liquid flow velocity greater than 150 cm/hour.

15. The adsorptive bed of claim 12, wherein each of the plurality of open cells has a characteristic diameter at least ten times larger than the characteristic diameter of the plurality of adsorptive beads.

16. The adsorptive bed of claim 12, wherein each of the plurality of adsorptive beads has a diameter of less than 100 microns.

* * * * *